United States Patent
Young et al.

(10) Patent No.: US 12,123,763 B2
(45) Date of Patent: Oct. 22, 2024

(54) LOAD SENSOR ASSEMBLY FOR BED LEG AND BED WITH LOAD SENSOR ASSEMBLY

(71) Applicant: Sleep Number Corporation, Minneapolis, MN (US)

(72) Inventors: Steven Jay Young, Los Gatos, CA (US); Carl Hewitt, San Jose, CA (US); Jonathan M. Olson, San Jose, CA (US); Alan Luckow, Ben Lomond, CA (US)

(73) Assignee: Sleep Number Corporation, Minneapolis, MN (US)

(*) Notice: Subject to any disclaimer, the term of this patent is extended or adjusted under 35 U.S.C. 154(b) by 0 days.

(21) Appl. No.: 17/876,229

(22) Filed: Jul. 28, 2022

(65) Prior Publication Data
US 2022/0364905 A1    Nov. 17, 2022

Related U.S. Application Data

(63) Continuation of application No. 16/549,367, filed on Aug. 23, 2019, now abandoned.
(Continued)

(51) Int. Cl.
*G01G 19/44* (2006.01)
*A47C 19/02* (2006.01)
(Continued)

(52) U.S. Cl.
CPC .......... *G01G 19/445* (2013.01); *A47C 19/027* (2013.01); *A47C 19/22* (2013.01);
(Continued)

(58) Field of Classification Search
CPC ...... G01G 19/445; G01G 19/52; G01G 21/02; G06N 20/00; G06N 5/04; A47C 19/22;
(Continued)

(56) References Cited

U.S. PATENT DOCUMENTS

| 411,343 A | 9/1889 | Leckron |
| 2,990,899 A | 7/1961 | De Bella |

(Continued)

FOREIGN PATENT DOCUMENTS

| AU | 2012101423 | 10/2012 |
| DE | 2020/07019717 | 11/2016 |

(Continued)

OTHER PUBLICATIONS

Computer translation of WO 2018079403 downloaded Jun. 3, 2024.*

(Continued)

*Primary Examiner* — Randy W Gibson
(74) *Attorney, Agent, or Firm* — Fish & Richardson P.C.

(57) ABSTRACT

A bed comprises substrate support members, each including a load bearing and a base configured to provide contact with a floor. The load bearing member is configured to move vertically relative to the base, while the base and the load bearing member are configured to fit together to maintain lateral alignment of the base and the load bearing member. A load sensor is positioned between the base and the load bearing member, the load bearing member configured to transmit a load from the substrate to the load sensor. A printed circuit board is in communication with the load sensor. A controller is in communication with the printed circuit board of each substrate support member and is configured to receive and process data output by the printed circuit boards.

14 Claims, 13 Drawing Sheets

Related U.S. Application Data

(60) Provisional application No. 62/804,623, filed on Feb. 12, 2019.

(51) Int. Cl.

| | | |
|---|---|---|
| *A47C 19/22* | (2006.01) | |
| *A61B 5/00* | (2006.01) | |
| *A61B 5/0205* | (2006.01) | |
| *A61B 5/11* | (2006.01) | |
| *G01G 19/52* | (2006.01) | |
| *G01G 21/02* | (2006.01) | |
| *G01V 9/00* | (2006.01) | |
| *G05B 15/02* | (2006.01) | |
| *G06N 5/04* | (2023.01) | |
| *G06N 20/00* | (2019.01) | |
| *G08B 21/22* | (2006.01) | |
| *A61B 5/08* | (2006.01) | |

(52) U.S. Cl.
CPC .......... *A61B 5/0205* (2013.01); *A61B 5/1102* (2013.01); *A61B 5/1115* (2013.01); *A61B 5/4818* (2013.01); *A61B 5/6891* (2013.01); *A61B 5/6892* (2013.01); *A61B 5/7203* (2013.01); *A61B 5/7246* (2013.01); *A61B 5/725* (2013.01); *A61B 5/7267* (2013.01); *A61B 5/7278* (2013.01); *A61B 5/7282* (2013.01); *A61B 5/7415* (2013.01); *G01G 19/52* (2013.01); *G01G 21/02* (2013.01); *G01V 9/00* (2013.01); *G05B 15/02* (2013.01); *G06N 5/04* (2013.01); *G06N 20/00* (2019.01); *G08B 21/22* (2013.01); *A61B 5/0816* (2013.01); *A61B 2560/0223* (2013.01)

(58) Field of Classification Search
CPC ... A61B 5/1102; A61B 5/1115; A61B 5/6891; A61B 2560/0223; G01V 9/00
See application file for complete search history.

(56) References Cited

U.S. PATENT DOCUMENTS

| | | | |
|---|---|---|---|
| 3,287,745 A | | 11/1966 | Maddox |
| 3,338,323 A | | 8/1967 | Swersey |
| 3,360,032 A | | 12/1967 | Potter |
| 3,722,611 A | | 3/1973 | Tirkkonen |
| 4,023,633 A | | 5/1977 | Swersey et al. |
| 4,121,453 A | | 10/1978 | Levin et al. |
| 4,281,730 A | | 8/1981 | Swersey et al. |
| 4,551,882 A | | 11/1985 | Swersey et al. |
| 4,633,237 A | | 12/1986 | Tucknott et al. |
| 4,667,357 A | | 5/1987 | Fortune |
| 4,679,569 A | | 7/1987 | Lee |
| 4,793,428 A | | 12/1988 | Swersey |
| 4,974,692 A | | 12/1990 | Carruth et al. |
| 5,173,977 A | | 12/1992 | Carruth et al. |
| 5,184,112 A | | 2/1993 | Gusakov |
| 5,276,432 A | | 1/1994 | Travis |
| 5,393,935 A | | 2/1995 | Hasty et al. |
| 5,393,938 A | | 2/1995 | Bumbalough |
| 5,747,745 A | | 5/1998 | Neuman |
| 5,831,221 A | * | 11/1998 | Geringer .............. G01G 19/445 177/144 |
| 5,861,582 A | | 1/1999 | Flanagan et al. |
| 6,280,392 B1 | | 8/2001 | Yoshimi et al. |
| 6,639,157 B2 | * | 10/2003 | Sternberg .............. G01G 19/445 177/144 |
| 6,680,442 B1 | | 1/2004 | Rynd et al. |
| 6,761,683 B2 | | 7/2004 | Gryn et al. |
| 6,765,154 B2 | | 7/2004 | Sternberg |
| 6,822,571 B2 | | 11/2004 | Conway |
| 6,852,086 B2 | | 2/2005 | Atlas |
| 7,176,391 B2 | | 2/2007 | Metz et al. |
| 7,253,366 B2 | | 8/2007 | Bhai |
| 7,335,839 B2 | | 2/2008 | Metz et al. |
| 7,437,787 B2 | | 10/2008 | Bhai |
| 7,467,426 B1 | | 12/2008 | Jarmon |
| 8,048,005 B2 | | 11/2011 | Dixon et al. |
| 8,262,582 B2 | | 9/2012 | Kortelainen |
| 8,279,057 B2 | | 10/2012 | Hirose |
| 8,376,964 B2 | | 2/2013 | Park et al. |
| 8,444,558 B2 | | 5/2013 | Young et al. |
| 8,469,884 B2 | | 6/2013 | David et al. |
| 8,491,490 B2 | | 7/2013 | Ozaki et al. |
| 8,544,347 B1 | | 10/2013 | Berme |
| 8,672,853 B2 | | 3/2014 | Young |
| 8,821,418 B2 | | 9/2014 | Meger et al. |
| 8,984,687 B2 | | 3/2015 | Stusynski et al. |
| 9,013,313 B2 | | 4/2015 | Paine |
| 9,370,457 B2 | | 6/2016 | Nunn et al. |
| 9,383,251 B2 | | 7/2016 | Dixon et al. |
| 9,392,879 B2 | | 7/2016 | Nunn et al. |
| 9,445,751 B2 | | 9/2016 | Young et al. |
| 9,504,416 B2 | | 11/2016 | Young et al. |
| 9,506,106 B2 | | 11/2016 | Gough et al. |
| 9,510,688 B2 | | 12/2016 | Nunn et al. |
| 9,596,998 B2 | | 3/2017 | Muehlsteff et al. |
| 9,635,953 B2 | | 5/2017 | Nunn et al. |
| 9,679,462 B1 | | 6/2017 | Robertson |
| 9,770,114 B2 | | 9/2017 | Brosnan et al. |
| 9,844,275 B2 | | 12/2017 | Nunn et al. |
| 9,931,085 B2 | | 4/2018 | Young et al. |
| D818,383 S | | 5/2018 | Sato et al. |
| 10,058,467 B2 | | 8/2018 | Stusynski et al. |
| 10,092,242 B2 | | 10/2018 | Nunn et al. |
| 10,149,549 B2 | | 12/2018 | Erko et al. |
| 10,182,661 B2 | | 1/2019 | Nunn et al. |
| 10,201,234 B2 | | 2/2019 | Nunn et al. |
| 10,206,590 B2 | | 2/2019 | Meriheina |
| 10,251,490 B2 | | 4/2019 | Nunn et al. |
| 10,342,358 B1 | | 7/2019 | Palashewski et al. |
| 10,413,233 B2 | | 9/2019 | Meriheina |
| 10,441,086 B2 | | 10/2019 | Nunn et al. |
| 10,441,087 B2 | | 10/2019 | Karschnik et al. |
| 10,448,749 B2 | | 10/2019 | Palashewski et al. |
| 10,492,969 B2 | | 12/2019 | Stusynski et al. |
| 10,632,032 B1 | | 4/2020 | Stusynski et al. |
| 10,646,050 B2 | | 5/2020 | Nunn et al. |
| 10,674,832 B2 | | 6/2020 | Brosnan et al. |
| 10,716,512 B2 | | 7/2020 | Erko et al. |
| 10,729,255 B2 | | 8/2020 | Erko et al. |
| 10,736,432 B2 | | 8/2020 | Brosnan et al. |
| 10,750,875 B2 | | 8/2020 | Palashewski et al. |
| 10,827,846 B2 | | 11/2020 | Karschnik et al. |
| 10,881,219 B2 | | 1/2021 | Nunn et al. |
| 10,957,335 B2 | | 3/2021 | Demirli et al. |
| 10,959,535 B2 | | 3/2021 | Karschnik et al. |
| D916,745 S | | 4/2021 | Stusynski et al. |
| 10,980,351 B2 | | 4/2021 | Nunn et al. |
| 11,096,849 B2 | | 8/2021 | Stusynski et al. |
| 11,122,909 B2 | | 9/2021 | Palashewski et al. |
| 11,160,683 B2 | | 11/2021 | Nunn et al. |
| 11,206,929 B2 | | 12/2021 | Palashewski et al. |
| D954,725 S | | 6/2022 | Stusynski et al. |
| D968,436 S | | 11/2022 | Stusynski et al. |
| D975,121 S | | 1/2023 | Stusynski et al. |
| D1,000,464 S | | 10/2023 | Stusynski et al. |
| D1,018,476 S | | 3/2024 | Dixon et al. |
| 2002/0023785 A1 | * | 2/2002 | Sternberg .............. G01G 19/445 177/144 |
| 2002/0070867 A1 | | 6/2002 | Conway et al. |
| 2003/0140714 A1 | | 7/2003 | Barua et al. |
| 2003/0233034 A1 | | 12/2003 | Varri et al. |
| 2006/0129047 A1 | | 6/2006 | Ruotoistenmaki |
| 2006/0175097 A1 | | 8/2006 | Pirzada |
| 2007/0161917 A1 | | 7/2007 | Ozaki et al. |
| 2007/0191742 A1 | | 8/2007 | Park |
| 2008/0077020 A1 | | 3/2008 | Young et al. |
| 2010/0170043 A1 | | 7/2010 | Young et al. |
| 2011/0004435 A1 | | 1/2011 | Lindstrom et al. |
| 2011/0144455 A1 | | 6/2011 | Young et al. |

(56) References Cited

U.S. PATENT DOCUMENTS

| | | |
|---|---|---|
| 2012/0078573 A1* | 3/2012 | Kazuno ............... A61B 5/6892 |
| | | 702/173 |
| 2012/0184862 A1 | 7/2012 | Foo et al. |
| 2013/0135137 A1 | 5/2013 | Mulder et al. |
| 2013/0146371 A1 | 6/2013 | Shih |
| 2013/0174345 A1 | 7/2013 | Leu et al. |
| 2014/0069729 A1 | 3/2014 | Shih |
| 2014/0135635 A1 | 5/2014 | Vanderpohl |
| 2014/0277822 A1 | 9/2014 | Nunn et al. |
| 2014/0352060 A1 | 12/2014 | Hirose |
| 2015/0101870 A1* | 4/2015 | Gough ............... G01N 33/5011 |
| | | 177/210 R |
| 2015/0126818 A1 | 5/2015 | Fung et al. |
| 2015/0157258 A1 | 6/2015 | Beattie et al. |
| 2015/0238021 A1 | 8/2015 | Wassermann |
| 2015/0320229 A1 | 11/2015 | Edling et al. |
| 2016/0015184 A1 | 1/2016 | Nunn et al. |
| 2016/0051156 A1 | 2/2016 | Kim |
| 2016/0063846 A1 | 3/2016 | Lemire et al. |
| 2016/0235367 A1 | 8/2016 | Kolar et al. |
| 2016/0367039 A1 | 12/2016 | Young et al. |
| 2017/0065220 A1 | 3/2017 | Young et al. |
| 2017/0067774 A1* | 3/2017 | Gough ................. A61G 7/0527 |
| 2017/0128001 A1 | 5/2017 | Torre et al. |
| 2017/0143269 A1 | 5/2017 | Young et al. |
| 2017/0160709 A1 | 6/2017 | Yang |
| 2017/0312154 A1 | 11/2017 | Kubiak et al. |
| 2018/0008168 A1* | 1/2018 | Pearlman ............... A61B 5/002 |
| 2018/0098900 A1 | 4/2018 | Sato et al. |
| 2018/0132627 A1 | 5/2018 | Van Erlach |
| 2019/0053761 A1 | 2/2019 | Torre et al. |
| 2019/0069840 A1 | 3/2019 | Young et al. |
| 2019/0200777 A1 | 7/2019 | Demirli et al. |
| 2019/0201265 A1 | 7/2019 | Sayadi et al. |
| 2019/0201266 A1 | 7/2019 | Sayadi et al. |
| 2019/0201267 A1 | 7/2019 | Demirli et al. |
| 2019/0201268 A1 | 7/2019 | Sayadi et al. |
| 2019/0201270 A1 | 7/2019 | Sayadi et al. |
| 2019/0201271 A1 | 7/2019 | Grey et al. |
| 2019/0290147 A1 | 9/2019 | Persen |
| 2019/0328146 A1 | 10/2019 | Palashewski et al. |
| 2019/0328147 A1 | 10/2019 | Palashewski et al. |
| 2020/0060558 A1 | 2/2020 | Aleksov |
| 2020/0110194 A1* | 4/2020 | Young .................... G01G 19/52 |
| 2020/0158560 A1* | 5/2020 | Khair .................. G01G 23/3714 |
| 2020/0315367 A1 | 10/2020 | Demirli et al. |
| 2020/0336010 A1 | 10/2020 | Holmvik et al. |
| 2020/0337470 A1 | 10/2020 | Sayadi et al. |
| 2020/0359807 A1 | 11/2020 | Brosnan et al. |
| 2020/0367663 A1 | 11/2020 | Nunn et al. |
| 2020/0405070 A1 | 12/2020 | Palashewski et al. |
| 2020/0405240 A1 | 12/2020 | Palashewski et al. |
| 2021/0000261 A1 | 1/2021 | Erko et al. |
| 2021/0034989 A1 | 2/2021 | Palashewski et al. |
| 2021/0045541 A1 | 2/2021 | Nunn et al. |
| 2021/0068552 A1 | 3/2021 | Palashewski et al. |
| 2021/0112992 A1 | 4/2021 | Nunn et al. |
| 2021/0267380 A1 | 9/2021 | Stusynski |
| 2021/0282570 A1 | 9/2021 | Karschnik et al. |
| 2021/0289947 A1 | 9/2021 | Karschnik et al. |
| 2021/0314405 A1 | 10/2021 | Demirli et al. |
| 2021/0346218 A1 | 11/2021 | Stusynski et al. |
| 2022/0000273 A1 | 1/2022 | Palashewski et al. |
| 2022/0000654 A1 | 1/2022 | Nunn et al. |
| 2022/0031220 A1 | 2/2022 | Guidoboni |
| 2022/0225786 A1 | 7/2022 | Palashewski et al. |
| 2022/0265059 A1 | 8/2022 | Palashewski et al. |
| 2022/0305231 A1 | 9/2022 | Stusynski et al. |
| 2022/0346565 A1 | 11/2022 | Karschnik et al. |
| 2022/0354431 A1 | 11/2022 | Molina et al. |
| 2022/0386947 A1 | 12/2022 | Molina et al. |
| 2022/0395233 A1 | 12/2022 | Siyahjani et al. |
| 2023/0018558 A1 | 1/2023 | Demirli et al. |
| 2023/0035257 A1 | 2/2023 | Karschnik et al. |
| 2023/0037482 A1 | 2/2023 | Demirli et al. |
| 2023/0054736 A1 | 2/2023 | Holmvik et al. |
| 2023/0063373 A1 | 3/2023 | Young et al. |
| 2023/0142604 A1 | 5/2023 | Dixon et al. |
| 2023/0148762 A1 | 5/2023 | Karschnik et al. |
| 2023/0181104 A1 | 6/2023 | Johnston et al. |
| 2023/0190199 A1 | 6/2023 | Molina |
| 2023/0210256 A1 | 7/2023 | MacLachlan et al. |
| 2023/0210268 A1 | 7/2023 | Kirk et al. |
| 2023/0210269 A1 | 7/2023 | Hill et al. |
| 2023/0210274 A1 | 7/2023 | Hill et al. |
| 2023/0210275 A1 | 7/2023 | Hill et al. |
| 2023/0218093 A1 | 7/2023 | Nunn et al. |
| 2023/0255843 A1 | 8/2023 | Sayadi et al. |
| 2023/0363963 A1 | 11/2023 | Sayadi et al. |
| 2023/0380756 A1 | 11/2023 | Palashewski et al. |
| 2023/0404282 A1 | 12/2023 | Sayadi et al. |
| 2023/0404825 A1 | 12/2023 | Stusynski et al. |
| 2023/0412683 A1 | 12/2023 | Demirli et al. |
| 2024/0016302 A1 | 1/2024 | Brosnan et al. |
| 2024/0032705 A1 | 2/2024 | Nunn et al. |
| 2024/0041221 A1 | 2/2024 | Blomseth et al. |
| 2024/0041677 A1 | 2/2024 | Grey et al. |
| 2024/0091487 A1 | 3/2024 | Molina et al. |
| 2024/0138579 A1 | 5/2024 | Karschnik et al. |

FOREIGN PATENT DOCUMENTS

| | | |
|---|---|---|
| EP | 0218957 | 4/1987 |
| EP | 1635153 | 3/2008 |
| EP | 2805702 | 11/2014 |
| EP | 1937148 | 1/2015 |
| FI | 116097 | 9/2005 |
| GB | 2119528 | 11/1983 |
| JP | H07198224 | 3/1995 |
| JP | 2002-182270 | 6/2002 |
| JP | 2004-024370 | 1/2004 |
| JP | 4002905 | 11/2007 |
| JP | 2012-207798 | 10/2012 |
| JP | 2014-233485 | 12/2014 |
| JP | 2014-235090 | 12/2014 |
| KR | 20060092037 | 8/2006 |
| KR | 10-2011-0033102 | 3/2011 |
| KR | 10-2012-0045660 | 5/2012 |
| KR | 10-2012-0119684 | 10/2012 |
| KR | 20120119684 | 10/2012 |
| KR | 101798498 | 11/2017 |
| WO | WO 9917658 | 4/1999 |
| WO | WO 2007/042960 | 4/2007 |
| WO | WO 2011/009085 | 1/2011 |
| WO | WO 2013/181474 | 12/2013 |
| WO | WO 2015/008677 | 1/2015 |
| WO | WO 2015/089274 | 6/2015 |
| WO | WO 2017/199944 | 11/2017 |
| WO | WO 2018/079403 | 5/2018 |
| WO | WO 2020/102383 | 5/2020 |

OTHER PUBLICATIONS

A. Alivar et al., "Motion Detection in Bed-Based Ballistocardiogram to Quantify Sleep Quality," GLOBECOM 2017-2017 IEEE Global Communications Conference, Singapore, 2017, pp. 1-6.

A. M. Adami, A. Adami, C. M. Singer, T. L. Hayes and M. Pavel, "A System for Unobtrusive Monitoring of Mobility in Bed," 2008 11th IEEE International Conference on Computational Science and Engineering—Workshops, San Paulo, 2008, pp. 13-18.

A. M. Adami, M. Pavel, T. L. Hayes and C. M. Singer, "Detection of Movement in Bed Using Unobtrusive Load Cell Sensors," in IEEE Transactions on Information Technology in Biomedicine, vol. 14, No. 2, pp. 481-490, Mar. 2010.

A. M. Adami, T. L. Hayes and M. Pavel, "Unobtrusive monitoring of sleep patterns," Proceedings of the 25th Annual International Conference of the IEEE Engineering in Medicine and Biology Society (IEEE Cat. No. 03CH37439), Cancun, 2003, pp. 1360-1363 vol. 2.

(56) References Cited

OTHER PUBLICATIONS

Adami A, Hayes T, Pavel M, Singer C. Detection and Classification of Movements in Bed using Load Cells. Cont Proc IEEE Eng Med Biol Soc 2005; 2006:589-92.

Adami AM, Adami AG, Hayes TL, Pavel M, Beattie ZT. A Gaussian model for movement detection during sleep. Annu Int Cont IEEE Eng Med Biol Soc_ 2012; 2012:2263-6.

Adami AM, Adami AG, Schwarz G, Beattie ZT, Hayes TL. A subject state detection approach to determine rest-activity patterns using load cells. Annu Int Cont IEEE Eng Med Biol Soc. 2010; 2010:204-7.

Adami AM, Hayes TL, Pavel M, Adami AG. Comparison of load cells and wrist-actigraphy for unobtrusive monitoring of sleep movements_ Annu Int Cont IEEE Eng Med Biol Soc. 2009; 2009:1314-7.

Adami AM, Pavel M, Hayes TL, Adami AG, Singer C. A method for classification of movements in bed. Annu Int Conf IEEE Eng Med Biol Soc_ 2011 ;2011 :7881-4.

Adami, Adriana & Adami, Andre & Hayes, T.L. & Beattie, Z.T.. (2014). Using load cells under the bed as a non-contact method for detecting periodic leg movements. IRBM. 35. 10.1016/j.irbm.2014; 1 page.

Adami, Adriana M., Andre Gustavo Adami, T. Hayes and Zachary T. Beattie; Unobtrusive Movement Detection during Sleep based on Load Cell Dynamics; (2013).; 9 pages.

Adami, Adriana Miorelli; Assessment and Classification of Movements in Bed Using Unobtrustive Sensors Dissertation; ProQuest Information and Learning Company; Aug. 2006; 24 pages.

Alibaba.com Website; GPB200 hospital bed high accuracy load cell in stock 300kg; https://galoce.en.alibaba.com/Product/62563162141-802678628/GPB200 hospital_bed_high_accuracy_load_eel1_in stock_300kg. html; accessed Nov. 2020.

Alihanka et al.; A new method for long-term monitoring of the ballistocardiogram, heart rate, and respiration; American Journal of Physiology-Regulatory, Integrative and Comparative Physiology; 1981; R384-R392.

Arslan et al., Instrumentation for Ballistocardiography; Aalto University School of Engineering ELEC-E8003 Project work course, year 2016; 19 pages.

Austin, Daniel et al. "Unobtrusive classification of sleep and wakefulness using load cells under the bed." Annual International Conference of the IEEE Engineering in Medicine and Biology Society. IEEE Engineering in Medicine and Biology Society. Annual International Conference vol. 2012 (2012): 5254-7.

B. Chamadiya et al., Textile-Based, Contactless ECG Monitoring for Non-ICU Clinical Settings, Journal of Ambient Intelligence and Humanized Computing, Jul. 2012, 11 pages.

Beattie et al., Classification of Breathing Events Using Load Cells under the Bed, Cont Proc IEEE Eng Med Biol Soc. 2009; 2009: 3921-3924.

Beattie ZT, Hagen CC, Hayes TL Classification of lying position using load cells under the bed. Annu Int Conf IEEE Eng Med Biol Soc. 2011; 2011:474-7.

Beattie ZT, Hagen CC, Pavel M, Hayes TL. Classification of breathing events using load cells under the bed. Annu Int Cont IEEE Eng Med Biol Soc. 2009; 2009:3921-4.

Beattie ZT, Hayes TL, Guilleminault C, Hagen CC. Accurate scoring of the apnea-hypopnea index using a simple noncontact breathing sensor. J Sleep Res. Jun. 2013;22(3):356-62.

Beattie ZT, Jacobs PG, Riley TC, Hagen CC. A time-frequency respiration tracking system using non-contact bed sensors with harmonic artifact rejection. Annu Int Cont IEEE Eng Med Biol Soc. Aug. 2015; 2015:8111-4.

Bio-Physical Signal, Advanced Biometric Research Center, Department of Biomedical Engineering, College of Medicine, Seoul National University, 2015, 4 pages. http://abrc.snu.ac.kr/korean/viewtopic.php?p=4039.

Braunstein, J R et al. "Design of a two-dimensional ballistocardiograph." The Journal of clinical investigation vol. 29.9 (1950): 1219-26.

Brink, M., Muller, C.H. & Schierz, C. Contact-free measurement of heart rate, respiration rate, and body movements during sleep_ Behavior Research Methods 38, 511-521 (2006).

Brotmacher L. The normal ballistocardiogram. Br Heart J. Apr. 1956;18(2):145-52.

Carlson C, Suliman A, Prakash P, Thompson D, Shangxian Wang, Natarajan B, Warren S. Bed-based instrumentation or unobtrusive sleep quality assessment in severely disabled autistic children. Annu Int Cont IEEE Eng Med Biol Soc. Aug. 2016 2016 :4909-4912.

Carlson, Charles; Development of a bed-based nighttime monitoring toolset Dissertation; Kansas State University; May 2019; 154 pages; https://krex.k-state.edu/dspace/handle/2097/39650.

Choi BH, Chung GS, Lee JS, Jeong DU, Park KS. Slow-wave sleep estimation on a load-cell-installed bed: a non-constrained method. Physiol Meas. Nov. 2009; 30(11):1163-70.

Choi BH, Seo JW, Choi JM, Shin HB, Lee JY, Jeong DU, Park KS. Non-constraining sleep/wake monitoring system using bed actigraphy_ Med Biol Eng Comput. Jan. 2007;45(1):107-14.

Chung GS, Choi BH, Jeong DU, Park KS. Noninvasive heart rate variability analysis using loadcell-installed bed during sleep_ Annu Int Cont IEEE Eng Med Biol Soc. 2007; 2007:2357-60.

Chung GS, Lee JS, Hwang SH, Lim YK, Jeong DU, Park KS. Wakefulness estimation only using ballistocardiogram: nonintrusive method for sleep monitoring_ Annu Int Cont IEEE Eng Med Biol Soc. 2010;2010:2459-62.

D. W_ Jung, S. H_ Hwang, H_N. Yoon, Y. G. Lee, D. Jeong and K. S. Park, "Nocturnal Awakening and Sleep Efficiency Estimation Using Unobtrusively Measured Ballistocardiogram," in IEEE Transactions on Biomedical Engineering, vol. 61,No. 1, pp. 131-138,Jan. 2014.

Di Lecce, v & Guaragnella, Cataldo & D'Orazio, T. & dario, r. (2013). Smart Postural Monitor for Elderly People. 4 pages.

Extended European Search Report in European Appln No. 19870848. 9, dated Mar. 20, 2023, 13 pages.

GAloce Website: Medical Bed Weighing Solution: https://www.galoce.com/industry/medical-apparatus/58.html; accessed Nov. 2020.

Gordon JW. Certain Molar Movements of the Human Body produced by the Circulation of the Blood. J Anal Physiol. 1877;11(Pt 3):533-536.

Harold W. March; Three-Plane Ballistocardiography: The Effect of Age on the Longitudinal, Lateral, and Dorsoventral Ballistocardiograms; Circulation. 1955; 12:869-882; 14 pages.

Hillrom Parts website; Bed Load Cell; https://direct.hillrom.com/hillromUS/en/Parts/Sensors/LOAD-CELUp/432B4900-1303-4AD6-B858-32A517599AC6; accessed Nov. 2020.

International Search Report and Written Opinion of corresponding application PCT/US2019/048219; dated Dec. 17, 2019; 12 pages.

International Search Report and Written Opinion of corresponding application PCT/US2019/047899; dated Dec. 16, 2019; 12 pages.

International Search Report and Written Opinion of corresponding International Application No. PCT/US2019/055121; dated Jan. 23, 2020; 11 pages.

J Alihanka, K Vaahtoranta, A static charge sensitive bed. A new method for recording body movements during sleep, Electroencephalography and Clinical Neurophysiology, vol. 46, Issue 6, 1979, pp. 731-734.

J. E. Mietus, C. K. Peng, P. C. Ivanov and A. L. Goldberger, "Detection of obstructive sleep apnea from cardiac interbeat interval time series," Computers in Cardiology 2000. vol. 27 (Cat. 00CH37163), Cambridge, MA, 2000, pp. 1753-1756.

J. Su, X. Zhu, X. Zhang, J. Tang and L Liu, "Ballistocardiogram Measurement System Using Three Load-Cell Sensors Platform in Chair," 2009 2nd International Conference on Biomedical Engineering and Informatics, Tianjin, 2009, pp. 1-4.

Jung DW, Hwang SH, Chung GS, Lee YJ, Jeong DU, Park KS. Estimation of sleep onset latency based on the blood pressure regulatory reflex mechanism. IEEE J Biomed Health Inform_ May 2013;17{3):534-44.

K. Watanabe, Y. Kurihara and H_ Tanaka, "Ubiquitous Health Monitoring at Home—Sensing of Human Biosignals on Flooring, on Tatami Mat, in the Bathtub, and in the Lavatory," in IEEE Sensors Journal, vol. 9, No. 12, pp. 1847-1855, Dec. 2009.

(56) References Cited

OTHER PUBLICATIONS

Kim, CS., Ober, S., McMurtry, M_ et al. Ballistocardiogram: Mechanism and Potential for Unobtrusive Cardiovascular Health Monitoring_ Sci Rep 6, 31297 (2016).

Lee et al., Physiological Signal Monitoring Bed for Infants Based on Load-Cell Sensors, Sensors, 2016, 16,409, 19 pages.

Lee WK, Yoon H, Han C, Joo KM, Park KS. Physiological Signal Monitoring Bed for Infants Based on Load-Cell Sensors_ Sensors (Basel). 2016;16(3):409. Published Mar. 19, 2016, 19 pages.

Lee WK, Yoon H, Jung DW, Hwang SH, Park KS. Ballistocardiogram of baby during sleep_ Annu Int Conf IEEE Eng Med Biol Soc. 2015;2015:7167-70.

Load Cell Central website; Hospital Beds, Portable Carts, Table Load Cell System; https://www.800loadcel.com/special-applications/other-specialized-systems/custom-load-cell-5.html; accessed Nov. 2020.

Loadstar Sensors Website; Monitor Sleep Patters; https://www.loadstarsensors.com/monitor-sleep-pattems.html, accessed Nov. 2020.

M. Alaziz, Z. Jia, J_ Liu, R. Howard, Y. Chen and Y. Zhang, "Motion Scale: A Body Motion Monitoring System Using Bed-Mounted Wireless Load Cells," 2016 IEEE First International Conference on Connected Health: Applications, Systems and Engineering Technologies (CHASE), Washington, DC, 2016, pp. 183-192.

M. Nagura, Y. Mitsukura, T. Kishimoto and M. Mimura, "A practical BCG measuring system with bed sensors and algorithm for heartbeat detection," 2018 IEEE 15th International Workshop on Advanced Motion Control (AMC), Tokyo, 2018, pp. 317-321.

M. Nagura, Y. Mitsukura, T. Kishimoto and M. Mimura, "An estimation of heart rate variability from ballistocardiogram measured with bed leg sensors," 2018 IEEE International Conference on Industrial Technology (ICIT), Lyon, 2018, pp. 2005-2009.

MSEC Website; Seca Platform Scale for Gurneys or Stretchers; https://ldiagnostic-supplies.medical-suppliesequipment-company_com/product/seca-platform-scale-for-gurneys-or-stretchers_9229.html; accessed Nov. 2020.

Muller, Christper; Projekt NEMESIS Niederfrequente elektrische und magnetische Felder und Elektrosensibilitat in der Schweiz; Doctoral Thesis; 2000; ETH Zurich Research collection; 258 pages with translation.

Nehmer el al., The Intelligent Bed—Ambient Monitoring of Sick and Disabled Persons through the Use of Load Sensors in Bed Legs, ERCIM News 87, Oct. 13, 2011, pp. 26-27, https://ercim-news.ercim.eu/en87/special/thentelligent-bed.

Nehmer et al., The Intelligent Bed—Ambient Monitoring of Sick and Disabled Persons through the Use of Load Sensors in Bed Legs; ERCIM News; 87; Oct. 2, 2011; 2 pages.

Nihon Kohden website—History—1950's, product—MB-1 Ballistocardiograph, Uses 1953; https://www.nihonkohden.com/company/history/1950s.html; accessed Nov. 2020.

Noh, Yun-Hong & Kew, Hsein Ping & Jeong, Doun. (2009). BCG Monitoring System using Unconstrained Method with Daubechies Wavelet Transform; Inter. Cont. on IML 2009; 338-344.

P W. Aung Aung et al., "Evaluation and analysis of multimodal sensors for developing in and around the bed patient monitoring system," 2010 Annual International Conference of the IEEE Engineering in Medicine and Biology, Buenos Aires,2010,pp. 2159-2162.

PartsSource Website; Bed Scale Load Cell Kit by Datex-Ohmeda; https://www.partssource.com/parts/datex-Phmeda/M1131131/ps68jdekdaq; accessed Nov. 2020.

Pinheiro, Eduardo & Postolache, 0. & Girao, P .. (2012). Study on Ballistocardiogram Acquisition in a Moving Wheelchair with Embedded Sensors. Metrology and Measurement Systems. 19. 739-750.

RICOH Website; Bed Sensor announced 2017; https://www.ricoh.com/about/empowering-digital-workplaces/articles/innovations-vital-to-enhancing-long-term-care; accessed Nov. 2020.

Rosales L, Skubic M, Heise D, Devaney MJ, Schaumburg M. Heartbeat detection from a hydraulic bed sensor using a clustering approach. Annu Int Cont IEEE Eng Med Biol Soc. 2012; 2012:2383-7.

S. Nukaya, T. Shino, Y. Kurihara, K. Watanabe and H. Tanaka, "Noninvasive Bed Sensing of Human Biosignals Via Piezoceramic Devices Sandwiched Between the Floor and Bed," in IEEE Sensors Journal, vol. 12, No. 3, pp. 431-438.

Sadek, I., Biswas, J. & Abdulrazak, B. Ballistocardiogram signal processing: a review. Health Inf Sci Syst 7, 10 (2019).

Schrempf A, Schossleitner G, Blaha A, Leipold S. Measuring nightly activity, body weight and body weight change rate with a sensor equipped bed. Annu Int Cont IEEE Eng Med Biol Soc. 2010; 2010:2151-4.

Sensotech Website; Patient Monitoring Sensors—Load Cell for Bed Weighing; https://www.sensomaticloadcell.in/patient-monitoring-sensor.html; accessed Nov. 2020.

Shin JH, Choi BH, Lim VG, Jeong DU, Park KS. Automatic ballistocardiogram (BCG) beat detection using a template matching approach_ Annu Int Cont IEEE Eng Med Biol Soc. 2008;2008:1144-6.

Starr et al., Twenty-Year Studies with the Ballistocardiograph: The Relation between the Amplitude of the First Record of "Healthy" Adults and Eventual Mortality and Morbidity from Heart Disease; Circulation 1961 ;23:714-732.

Stryker Maintenane Manual; MedSurge Bed Model 3002 S3 Patriot Series; Oct. 2008; 227 pages; https://techweb.stryker.com/MedSurg/3002S3/0806/maintenance/patriot/3006-009-102C .pdf.

Talbot et al., Dynamic Comparison of Current Ballistocardiographic Methods: Part I: Artefacts in the Dynamically Simple Ballistocardiographic Methods; Circulation. 1955; 12:577-587.

TE Connectivity Website; Bed Load Cell White Paper for Patient beds; https://www.le.com/usa-en/industries/sensorsolutions/insights/compact-load-cell-design-white-paper_html; accessed Nov. 2020.

VPG Transducers; Medical Beds; https://vpgtransducers.com/markets/medical; accessed Nov. 2020.

Williams, James; MIT; This 30-ppm Scale Proves that Analog Designs Aren't Dead Yet; Oct. 5, 1976; 4 pages; https://m.eel.com/media/1117151/1976-10-05 _30ppmscale.pdf.

Zemic website; Medical hospital bed uses modified Zemic HBC loadcell; https://www.zemiceurope.com/en/casestudiesNitalgo_TLB medical hospital bed uses Zemic_Loadcells/; accessed Nov. 2020.

U.S. Appl. No. 16/719,177, Nunn et al., filed Dec. 18, 2019.
U.S. Appl. No. 17/745,508, Nunn et al., filed May 16, 2022.
U.S. Appl. No. 18/389,388, Johnston et al., filed Nov. 14, 2023.
U.S. Appl. No. 18/404,647, Palashewski et al., filed Jan. 4, 2024.
U.S. Appl. No. 18/416,387, Nunn et al., filed Jan. 18, 2024.
U.S. Appl. No. 18/433,289, Demirli et al., filed Feb. 5 2024.
U.S. Appl. No. 18/538,884, Palashewski et al., filed Dec. 13, 2023.
U.S. Appl. No. 18/602,407, Holmvik et al., filed Mar. 12, 2024.
U.S. Appl. No. 18/604,949, Palashewski et al., filed Mar. 14, 2024.
U.S. Appl. No. 18/639,292, Mayandi et al., filed Apr. 18, 2024.
U.S. Appl. No. 18/643,648, Sohn et al., filed Apr. 23, 2024.
U.S. Appl. No. 29/881,955, Stusynski et al., filed Jan. 9, 2023.
U.S. Appl. No. 29/910,800, Stusynski et al., filed Aug. 24, 2023.
U.S. Appl. No. 29/924,373, Dixon et al., filed Jan. 18, 2024.

* cited by examiner

LOAD SENSOR ASSEMBLY FOR BED LEG AND BED WITH LOAD SENSOR ASSEMBLY

CROSS-REFERENCE TO RELATED APPLICATION(S)

This application is a continuation application of U.S. patent application Ser. No. 16/549,367, filed Aug. 23, 2019, which claims the benefit of U.S. Provisional Patent Application Ser. No. 62/804,623, filed Feb. 12, 2019, the entire disclosure of which is hereby incorporated by reference.

TECHNICAL FIELD

This disclosure relates to systems and methods for sensing biometrics and other subject-specific information of one or more subjects using multiple sensors that are positioned in or replace a bed leg.

BACKGROUND

Sensors have been used to detect heart rate, respiration and presence of a single subject using ballistocardiography and the sensing of body movements using noncontact methods, but are often not accurate at least due to their inability to adequately distinguish external sources of vibration and distinguish between multiple subjects. In addition, the nature and limitations of various sensing mechanisms make it difficult or impossible to accurately determine a subject's biometrics, presence, weight, location and position on a bed due to factors such as air pressure variations or the inability to detect static signals.

SUMMARY

Disclosed herein are implementations of load sensor assemblies for beds.

One embodiment of a load sensor assembly for a substrate that supports a subject comprises at least four substrate support members, wherein each of the four substrate support members comprises: a load bearing member configured to be attached to the substrate at a first end of the load bearing member; a base configured to support the load bearing member and to provide contact with a floor, wherein the load bearing member is configured to move vertically relative to the base; a load sensor between the cap and the base, wherein the load bearing member is configured to transmit a load from the substrate to the load sensor; and a printed circuit board positioned in a cavity defined by one of the base or the load bearing member and in communication with the load sensor, wherein the printed circuit board is configured to receive and process data from the load sensor.

Another embodiment of a load sensor assembly is a sensor cartridge for use with a bed having legs to support the bed, the cartridge comprising a base having a first end portion and a second end portion opposite the first end portion, wherein the base is configured to provide contact with a floor at the first end portion; a load bearing member engaged with the second end portion of the base, wherein the base and the load bearing member are configured to fit together to maintain lateral alignment of the cap to the base while allowing vertical movement of the load bearing member with respect to the base; and a load sensor between the load bearing member and the base, wherein the load bearing member is configured to transmit the load from the substrate to the load sensor. A printed circuit board is positioned within a cavity defined by one of the load bearing member or the base, the printed circuit board in communication with the load sensor and configured to receive and process data from the load sensor, wherein the sensor cartridge is configured to insert into a leg of the bed that is at least partially hollow.

Another embodiment of a load sensor assembly is a bed having a frame supporting a substrate configured to support a subject, the bed comprising substrate support members. Each substrate support member comprises a load bearing member having a first end portion and a second end portion and a base configured to provide contact with a floor. The load bearing member is configured to move vertically relative to the base and the base and the load bearing member are configured to fit together to maintain lateral alignment of the base and the load bearing member. A load sensor is positioned between the load bearing member and the base, wherein the load bearing member is configured to transmit a load from the substrate to the load sensor. A printed circuit board is in communication with the load sensor and is configured to receive and process data from the load sensor. A controller is in communication with the printed circuit board of each substrate support member, wherein the controller is configured to receive and process data output by the printed circuit boards.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
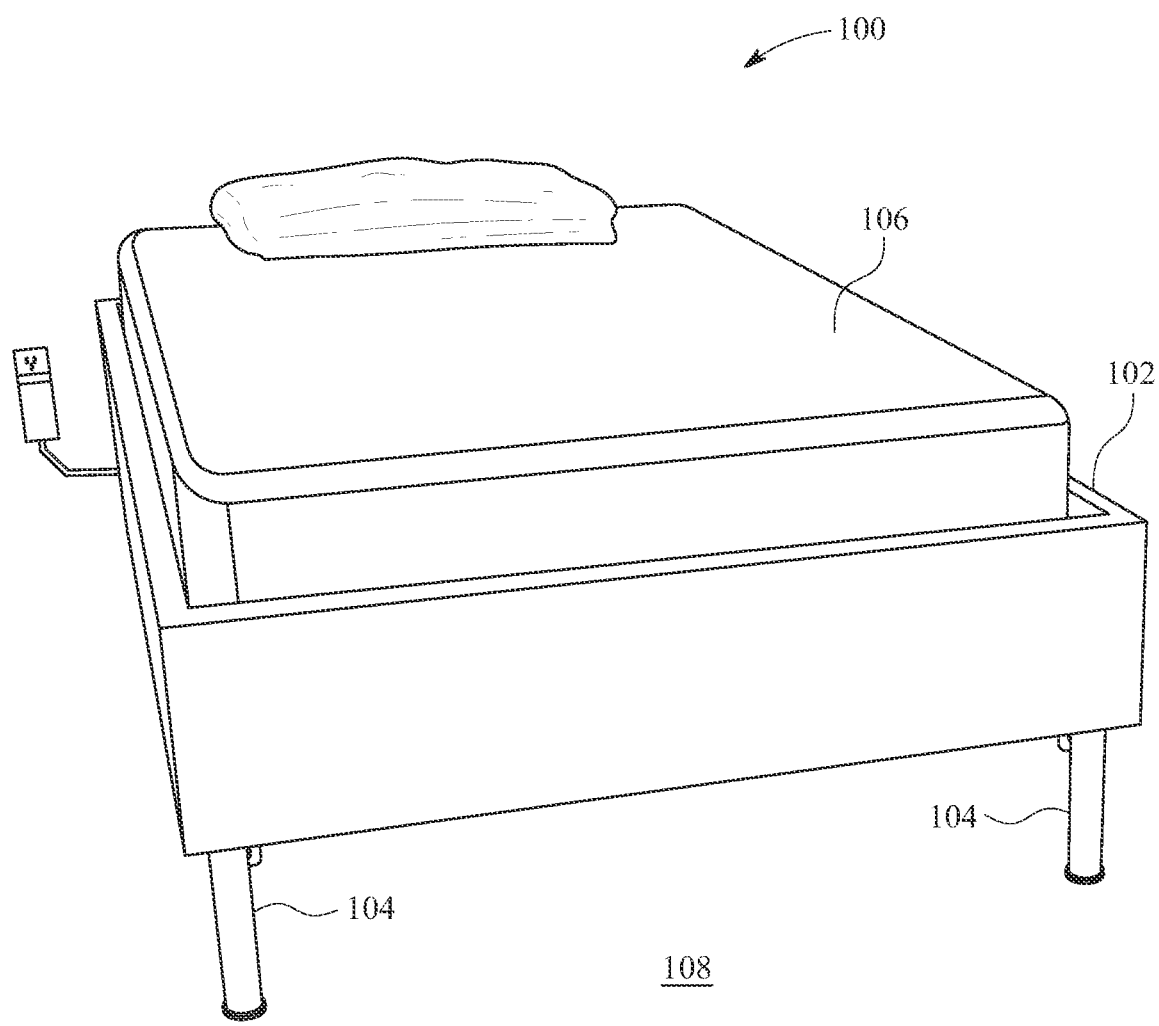
FIG. 1 is an illustration of a bed incorporating the load sensor assembly as disclosed herein.

Disclosed herein are implementations of systems and methods employing gravity and motion to determine biometric parameters and other person-specific information for single or multiple subjects at rest and in motion on one or multiple substrates. The systems and methods use multiple sensors to sense a single subject's or multiple subjects' body motions against the force of gravity on a substrate, including beds, furniture or other objects, and transforms those motions into macro and micro signals. Those signals are further processed and uniquely combined to generate the person-specific data, including information that can be used to further enhance the ability of the sensors to obtain accurate readings. The sensors are connected either with a wire, wirelessly or optically to a host computer or processor which may be on the internet and running artificial intelligence software. The signals from the sensors can be analyzed locally with a locally present processor or the data can be networked by wire or other means to another computer and remote storage that can process and analyze the real-time and/or historical data.

The sensors are designed to be placed under, or be built into a substrate, such as a bed, couch, chair, exam table, floor, etc. The sensors can be configured for any type of surface depending on the application. Additional sensors can be added to augment the system, including light sensors, temperature sensors, vibration sensors, motion sensors, infrared sensors and sound sensors as non-limiting examples. Each of these sensors can be used to improve accuracy of the overall data as well as provide actions that can be taken based on the data collected. Example actions might be: turning on a light when a subject exits a bed, adjusting the room temperature based on a biometric status, alerting emergency responders based on a biometric status, sending an alert to another alert based system such as: Alexa, Google Home or Siri for further action.

The data collected by the sensors can be collected for a particular subject for a period of time, or indefinitely, and can be collected in any location, such as at home, at work, in a hospital, nursing home or other medical facility. A limited period of time may be a doctor's visit to assess weight and biometric data or can be for a hospital stay, to determine when a patient needs to be rolled to avoid bed sores, to monitor if the patient might exit the bed without assistance, and to monitor cardiac signals for atrial fibrillation patterns. Messages can be sent to family and caregivers and/or reports can be generated for doctors.

The data collected by the sensors can be collected and analyzed for much longer periods of time, such as years or decades, when the sensors are incorporated into a subject's personal or animal's residential bed. The sensors and associated systems and methods can be transferred from one substrate to another to continue to collect data from a particular subject, such as when a new bed frame is purchased for a residence or retrofitted into an existing bed or furniture.

The highly sensitive, custom designed sensors detect wave patterns of vibration, pressure, force, weight, presence and motion. These signals are then processed using proprietary algorithms which can separate out and track individual source measurements from multiple people, animals or other mobile or immobile objects while on the same substrate.

These measurements are returned in real-time as well as tracked over time. Nothing is attached to the subject. The sensors can be electrically or optically wired to a power source or operate on batteries or use wireless power transfer mechanisms. The sensors and the local processor can power down to zero or a low power state to save battery life when the substrate is not supporting a subject. In addition, the system may power up or turn on after subject presence is detected automatically.

The system is configured based on the number of sensors. Because the system relies on the force of gravity to determine weight, sensors are required at each point where an object bears weight on the ground. For other biometric signals fewer sensors may be sufficient. For example, a bed with four wheels or legs may require a minimum of four sensors, a larger bed with five or six legs may require five for six sensors, a chair with four legs would may require sensors on each leg, etc. The number of sensors is determined by the needed application. The unique advantage of multiple sensors provides the ability to map and correlate a subject's weight, position and bio signals. This is a clear advantage in separating out a patient's individual signals from any other signals as well as combining signals uniquely to augment the signals for a specific biosignal.

The system can be designed to configure itself automatically based on the number of sensors determined on a periodic or event-based procedure. A standard configuration would be four sensors per single bed with four legs to eight leg sensors for a multiple person bed. The system would automatically reconfigure for more or less sensors. Multiple sensors provide the ability to map and correlate a subject's weight, position and bio signals. This is necessary to separate multiple subjects' individual signals.

Some examples of the types of information that the disclosed systems and methods provide are dynamic center of mass and center of signal locations, accurate bed exit prediction (timing and location of bed exit), the ability to differentiate between two or more bodies on a bed, supine/side analysis, movement vectors for multiple subjects and other objects or animals on the bed, presence, motion, position, direction and rate of movement, respiration rate, respiration condition, heart rate, heart condition, beat to beat variation, instantaneous weight and weight trends, and medical conditions such as heart arrhythmia, sleep apnea, snoring, restless leg, etc. By leveraging multiple sensors that detect the z-axis and other axes of the force vector of gravity, and by discriminating and tracking the center of mass or center of signal of multiple people as they enter and move on a substrate, not only can the disclosed systems and methods determine presence, motion and cardiac and respiratory signals for multiple people, but they can enhance the signals of a single person or multiple people on the substrate by applying the knowledge of location to the signal received. Secondary processing can also be used to identify multiple people on the same substrate, to provide individual sets of metrics for them, and to enhance the accuracy and strength of signals for a single person or multiple people. For example, the system can discriminate between signals from an animal jumping on a bed, another person sitting on the bed, or another person lying in bed, situations that would otherwise render the signal data mixed. Accuracy is increased by processing signals differently by evaluating how to combine or subtract signal components from each sensor for a particular subject.

Additional sensor types can be used to augment the signal, such as light sensors, temperature sensors, accelerometers, vibration sensors, motion sensors and sound sensors. While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

FIG. 1 is a top perspective view of a bed 100 having a substrate 106 on which the subject can lie. The bed 100 includes a frame 102 which supports the substrate 106 (e.g. bedding, a mattress or a box-spring mattress foundation). The frame 102 may include internal or external channels configured to receive wiring. The bed 100 may include four sensor assemblies 104 attached to the frame 102. More or fewer sensor assemblies 104 may be attached to bed frames of varying shapes, sizes and configurations. Any point in which a load is transferred from the bed 100 to the floor may have an intervening sensor assembly 104. In other embodiments, the sensor assemblies 104 may be attached to and/or inserted into existing legs supporting the bed 100. In the illustrated, non-limiting example, one sensor assembly 104 is attached to each corner of the frame 102. The sensor assemblies 104 may extend from the frame 102 or an existing bed leg to a floor 108 used to support the bed 100. The floor can include the ground or any surface suitable to support the bed 100.

Figure 2A:
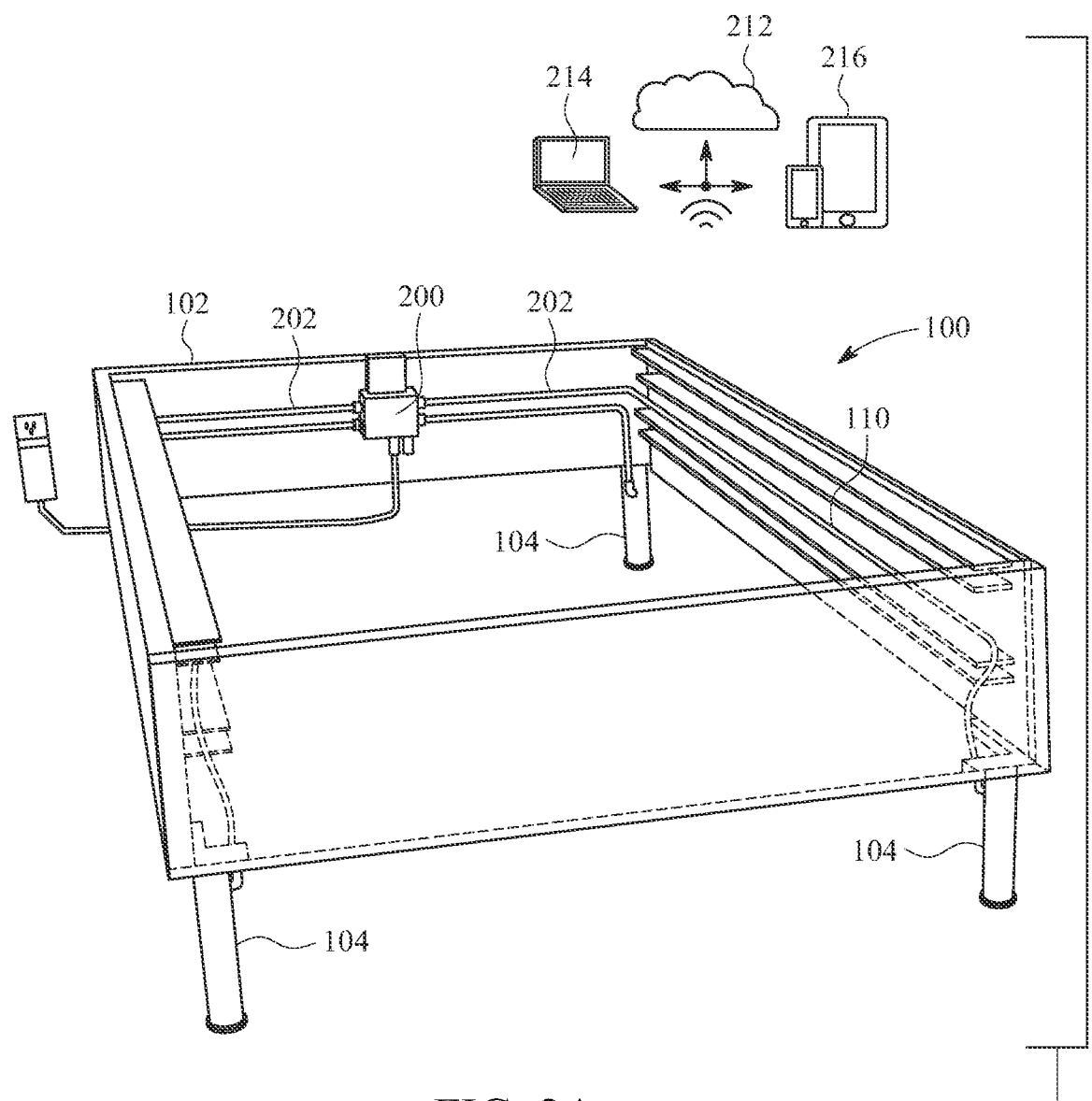
FIG. 2A is an illustration of the bed frame with the load sensor assembly incorporated, the bed frame configured to support a single subject.

FIG. 2A is a top perspective view of the frame 102 and sensor assemblies 104. A controller 200 can be wired or wirelessly connected to the sensor assemblies 104. Wiring 202 may electrically connect the sensor assemblies 104 to the controller 200. The wiring 202 may be attached to an interior of the frame 102 and/or may be routed through the interior channels 110 of the frame 102. The controller 200 can collect and process signals from the sensor assemblies 104. The controller 200 may also be configured to output power to the sensors and/or to printed circuit boards disposed in the sensor assemblies 104. The controller 200 can be attached to the frame 102 so that it is hidden from view, can be under the bed, or can be positioned anywhere a wire reaches the sensor assemblies 104 if transmission is hard wired. The controller 200 can be positioned anywhere a wireless transmission can be received from the sensor assemblies 104 if transmission is wireless. The controller 200 can be programmed to control other devices based on the processed data as discussed below, the control of other devices also being wired or wireless. Alternatively or in addition to, a cloud based computer 212 or off-site controller 214 can collect the signals directly from the sensor assemblies 104 for processing or can collect raw or processed data from the controller 200. For example, the controller 200 may process the data in real time and control other local devices as disclosed herein, while the data is also sent to the off-site controller 214 that collects and stores the data over time. The controller 200 or the off-site controller 214 may transmit the processed data off-site for use by downstream third parties such a medical professionals, fitness trainers, family members, etc. The controller 200 or the off-site controller 214 can be tied to infrastructure that assists in collecting, analyzing, publishing, distributing, storing, machine learning, etc. Design of real-time data stream processing has been developed in an event-based form using an actor model of programming. This enables a producer/consumer model for algorithm components that provides a number of advantages over more traditional architectures. For example, it enables reuse and rapid prototyping of processing and algorithm modules. As another example, it enables computation to be location-independent (i.e., on a single device, combined with one or more additional devices or servers, on a server only, etc.)

The long-term collected data can be used in both a medical and home setting to learn and predict patterns of sleep, illness, etc. for a subject. As algorithms are continually developed, the long-term data can be reevaluated to learn more about the subject. Sleep patterns, weight gains and losses, changes in heart beat and respiration can together or individually indicate many different ailments. Alternatively, patterns of subjects who develop a particular ailment can be studied to see if there is a potential link between any of the specific patterns and the ailment.

The data can also be sent live from the controller 200 or the off-site controller 214 to a connected device 216, which can be wirelessly connected for wired. The connected device 216 can be, as examples, a mobile phone or home computer. Devices can subscribe to the signal, thereby becoming a connected device 216.

Figure 2B:
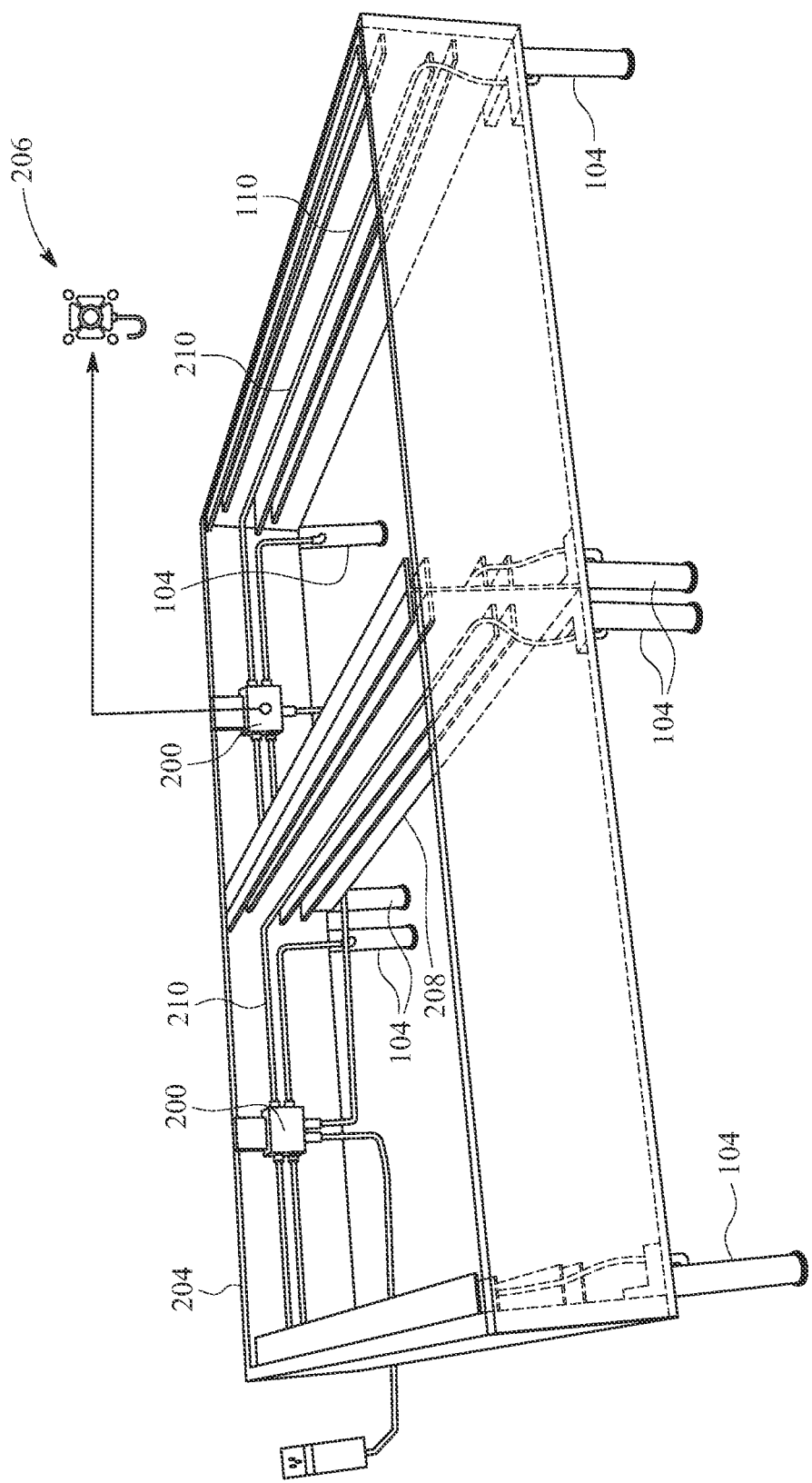
FIG. 2B is an illustration of a bed frame with the load sensor assembly, the bed frame configured to support two subjects.

FIG. 2B is a top perspective view of a frame 204 for a bed 206 used with a substrate on which two or more subjects can lie. The bed 206 may include features similar to those of the bed 100 except as otherwise described. The bed 206 includes a frame 204 configured to support two or more subjects. The bed 206 may include eight sensor assemblies 104, including one sensor assembly 104 disposed at each corner of the frame 204 and four sensor assemblies 104 disposed at opposing ends of a central frame member 208. In other embodiments, the bed may include nine sensor assemblies 104, including an additional sensor assembly 104 disposed at the middle of the central frame member 208. In other embodiments, the bed 206 may include any arrangement of sensor assemblies 104. Two controllers 200 can be attached to the frame 204. The controllers 200 may be in wired or wireless communication with its respective sensors and optionally with each other. Each of the controllers 200 collects and processes signals from a subset of sensor assemblies 104. For example, one controller 200 can collect and process signals from sensor assemblies 104 (e.g. four sensor assemblies) configured to support one subject lying on the bed 206. Another controller 200 can collect and process signals from the other sensor assemblies 104 (e.g. four sensor assemblies) configured to support the other subject lying on the bed 206. Wiring 210 may connect the sensor assemblies 104 to either or both of the controllers 200 attached to the frame 204. The wiring 210 may also connect the controllers 200. In other embodiments, the controllers may be in wireless communication with each other.

Figure 3:
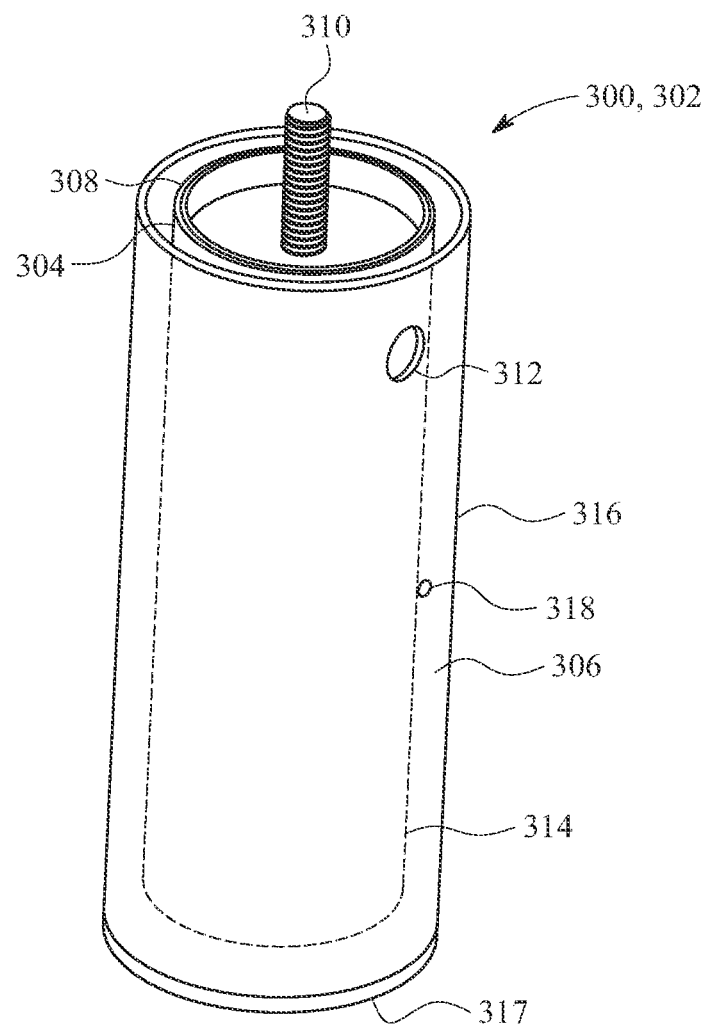
FIG. 3 is a top perspective view of a substrate support member as disclosed herein.

FIG. 3 is a top perspective view of a sensor assembly 300 according to one embodiment. The sensor assembly 300 includes multiple substrate support members 302 (one of which is shown in FIG. 3) configured to support a bed frame and/or substrate. The substrate support member 302 includes a load bearing member 304 engaging a base 306. The load bearing member 304 extends between the frame 102 and/or substrate 106 and the base 306. A sensor (e.g. load sensor 404 in FIG. 4) is disposed between the load bearing member 304 and the base 306. A first end 308 of the load bearing member 304 may include an attachment member 310 configured to be attached to the frame 102 and/or substrate 106. In the illustrated, non-limiting example, the attachment member 310 is a threaded member configured to be screwed into a bed frame. In other embodiments, the attachment member 310 may include a screw, bolt, or any other fastener.

The load bearing member 304 may be a substantially cylindrical tube, but may be any other shape or configuration. For example, the load bearing member 304 may be a rectangular tube with two or more walls, may be two or more columns, or any may be any other structure that adequately supports and evenly distributes the load from the frame and/or substrate to the sensor. The load bearing member 304 may be made of any wood, plastic, metal, any other suitable material, or any combination thereof. The load bearing member 304 may include an aperture 312 configured to allow wiring (not shown) to extend from an interior of the load bearing member 304 to an exterior of the load bearing member 304.

The base 306 supports the load bearing member 304 and is configured to provide contact with the floor (or ground) at an end of the base 306. A second end 314 of the load bearing member 304 is engaged with the base 306 such that vertical movement is allowed. The load bearing member 304 is configured to move vertically with respect to the base 306. This movement can be very slight but allows for transfer of various loads onto the sensor. The base 306 may be a sleeve 316 disposed around the load bearing member 304. The base 306 may also include a bottom portion 317 integral with or attached to the sleeve 316. The bottom portion 317 may be disposed between the sleeve 316 and the floor. The sleeve 316 may have an exterior profile shaped to represent a leg of the bed 100. The sleeve 316 may extend partially along a length of the load bearing member 304 or may extend along nearly an entire length of the load bearing member 304. The base 306 or sleeve 316 does not contact the frame and/or the substrate to ensure all load is transferred to the load bearing member 304. For example, the sleeve 316 may extend along a length of the load bearing member 304 sufficient to conceal the load bearing member 304 and to look to a subject proximate the bed that the sleeve 316 is a leg of the bed 100. The sleeve 316 may include a substantially cylindrical shape or any other shape. The base 306, the sleeve 316, and/or the bottom portion 317 may be made of any wood, plastic, metal, any other suitable material, or any combination thereof. The base 306 may include an aperture 318 configured to allow wiring (not shown) to extend from an interior of the base to an exterior of the base 306. The sleeve 316 can be separate from the base 306 and may be used to provide the aesthetics of a bed leg without being actually a part of the base 306 or load bearing member 304.

Figure 4:
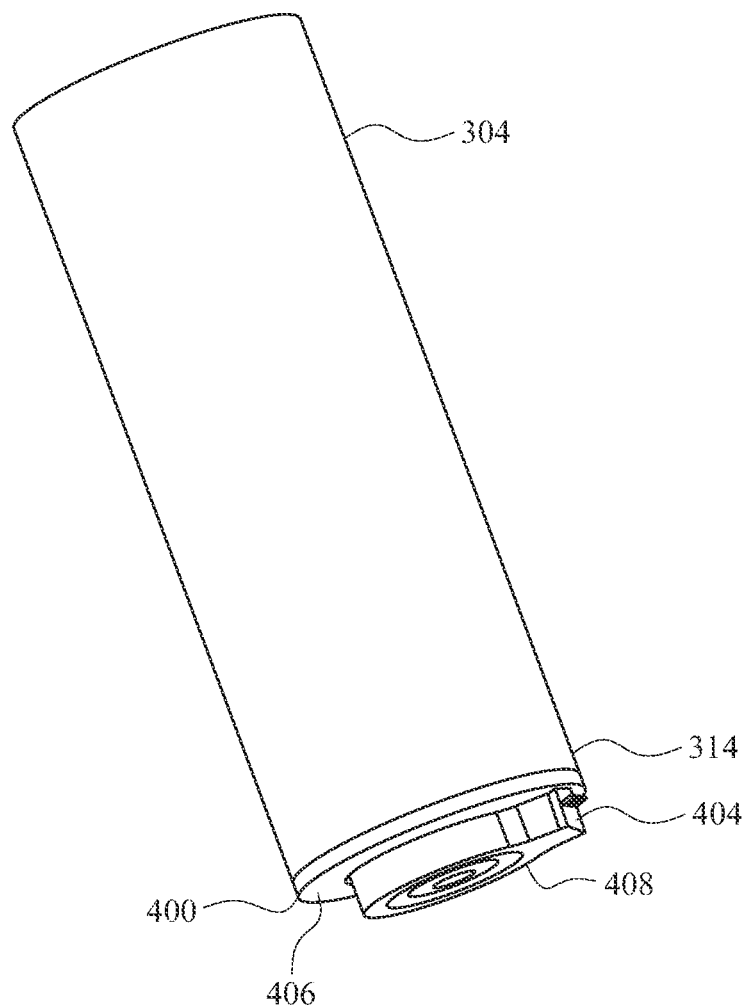
FIG. 4 is a bottom perspective view of a load bearing member and load sensor of the substrate support member of FIG. 3.

FIG. 4 is a bottom perspective view of the load bearing member 304. A cap 400 may be disposed proximate to the second end 314 of the load bearing member 304. For example, a portion of the cap 400 may be disposed inside the load bearing member 304. The cap 400 may be attached to the second end 314 of the load bearing member 304 via interference fit, adhesive, or any other means of attachment. The cap 400 can be integral with the load bearing member 304, such that it is simply an end of the load bearing member 304.

A load sensor 404 may be attached to a bottom surface 406 of the cap 400. In other embodiments, the load sensor 404 may be attached to an interior surface of the base 306 (e.g. to a top surface of the bottom portion 317). The load sensor 404 may be attached to the cap 400 and/or the base 306 via interference fit, adhesive, plastic welding, or any other means of attachment. The cap 400 may include a recess defined by the bottom surface of the cap 400. The recess may be configured to receive the load sensor 404. For example, an interior profile of the recess in the cap 400 may be shaped to correspond with an exterior profile of a portion of the load sensor 404. In this configuration, the load bearing member 304, the cap 400, and the load sensor 404 may be configured to fit together to maintain lateral, or radial, alignment of the load bearing member 304, the cap 400, and the load sensor 404 to maintain accurate transmission of the load to the load sensor 404.

Figure 5:
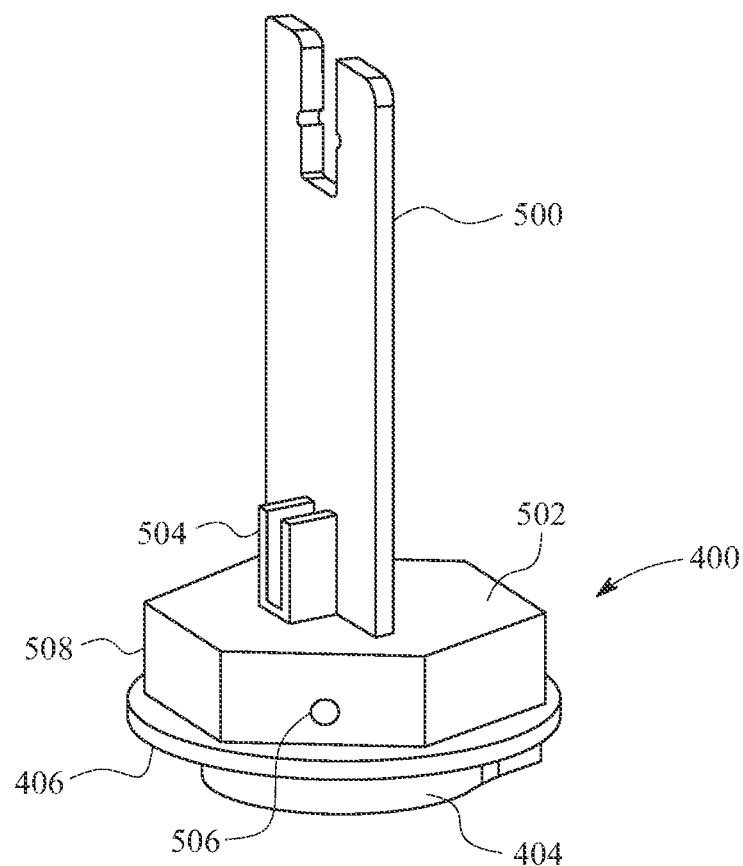
FIG. 5 is a top perspective view of a cap and printed circuit board of the substrate support member of FIG. 3.

In FIGS. 4 and 5, a bottom surface 408 of the load sensor 404 is configured to contact the bottom portion 317 of the base 306. As described later with respect to FIG. 6, the bottom portion 317 of the base 306 includes a contact member 604 that contacts the load sensor 404. Load from the subject on the substrate is transmitted through the load bearing member 304 with the contact member 604 providing the resistance, allowing the load sensor 404 to read the load. In this configuration, the base 306, the cap 400, the load bearing member 304, and the load sensor 404 are configured to fit together to maintain lateral alignment of the base 306, the cap 400, the load bearing member 304, and the load sensor 404. In other embodiments, the load sensor 404 may be attached to the bottom portion 317 with the contact member 604 provided on the bottom surface 406 of the cap 400.

FIG. 5 is a top perspective view of the cap 400 attached to a printed circuit board 500. The printed circuit board 500 may be attached to a top surface 502 of the cap 400 via a mount 504. The printed circuit board 500 may be attached to the cap 400 and/or the mount 504 using plastic welding, adhesive, or any other means of attachment. The printed circuit board 500 may be located inside the load bearing member 304 when the cap 400 is attached to the second end 314 of the load bearing member 304. The printed circuit board 500 may be in communication with the load sensor 404 and/or the controller 200 (e.g. via wired or wireless communication). The printed circuit board 500 may be configured to receive and process data from the load sensor 404. The cap 400 may include an aperture 506 through a portion of the cap 400. Wiring (not shown) may be routed through the aperture 506 from the load sensor 404 to the printed circuit board 500.

The cap 400 may optionally include a portion 508 configured to be disposed inside the load bearing member 304. The portion 508 may be shaped and sized to fit inside a cavity defined by the load bearing member 304 such that the cap 400 and the load bearing member 304 may be attached via interference fit between the portion 508 and the load bearing member 304. The printed circuit board 500 may be attached to the portion 508 of the cap 400.

Figure 6:
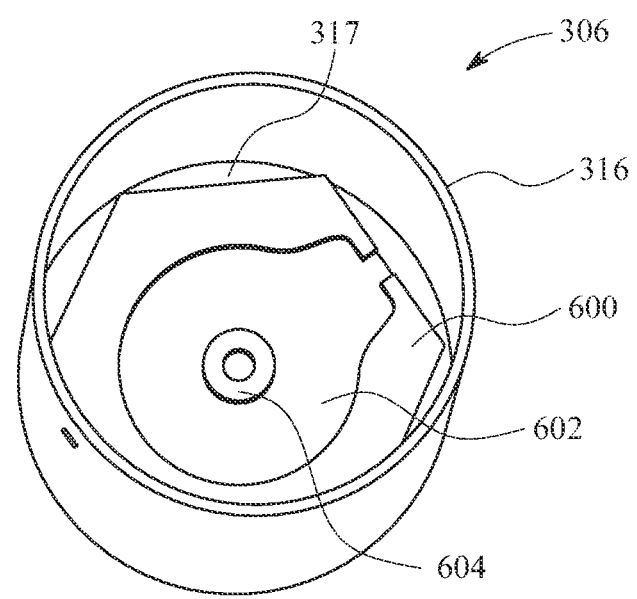
FIG. 6 is a top perspective view of a base of the substrate support member of FIG. 3.

FIG. 6 is a top perspective view of the base 306. In the illustrated, non-limiting example, the sleeve 316 is attached to the bottom portion 317. The bottom portion 317 may include a supporting member 600. The bottom portion 317 (e.g. the supporting member 600) may include a recess 602 shaped to receive the load sensor 404. The bottom portion 317 includes the contact member 604 configured to contact the load sensor 404. In other embodiments, the supporting member 600 may have be of a different shape and size.

Figure 7:
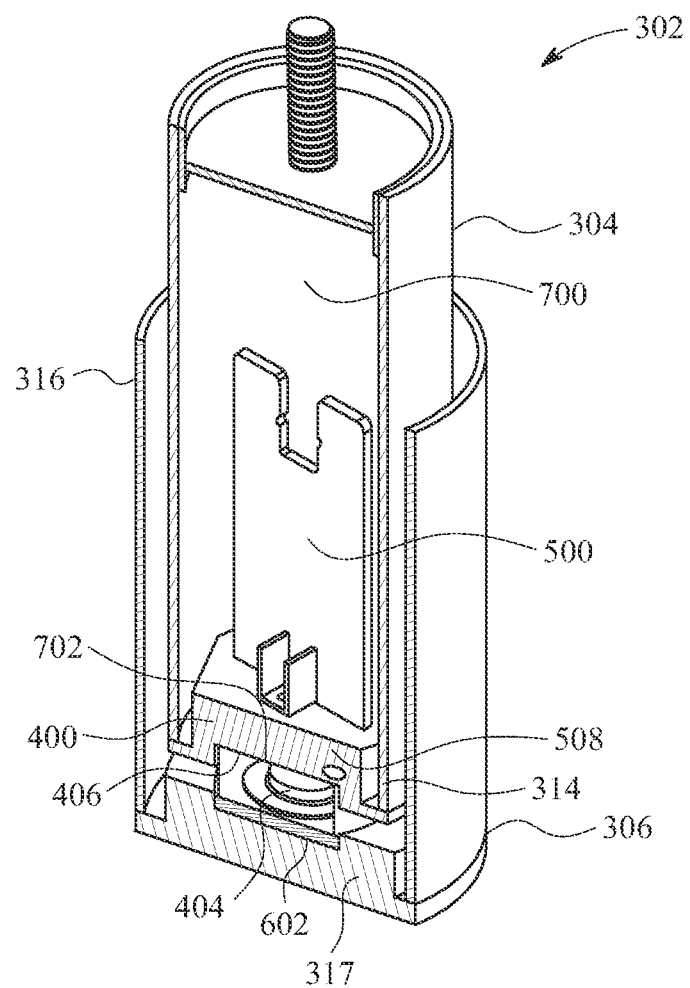
FIG. 7 is a cross-sectional view of the substrate support member of FIG. 3.

FIG. 7 is a cross sectional view of the substrate support member 302. The load bearing member 304 defines a cavity 700. The cap 400 is attached to the second end 314 of the load bearing member 304. The printed circuit board 500 attached to the cap 400 may be positioned in the cavity 700 of the load bearing member 304. The load sensor 404 is disposed between the cap 400 and the base 306. For example, the load sensor 404 may be disposed in the recess 602 of the bottom portion 317 of the base 306 and in a recess 702 defined by the cap 400. A bottom surface of the bottom portion 317 of the base 306 may contact the floor. One end of the sleeve 316 may contact a top surface of the bottom portion 317.

When the subject sits, lies, or moves on the substrate, a load is placed on the substrate. The load is transferred from the substrate to each load bearing member 304. The load bearing member 304 transfers the load to the load sensor 404. The load bearing member 304 and the cap 400 attached to the second end 314 of the load bearing member 304 may be configured to move vertically relative to the base 306 as the magnitude of the load on the substrate changes.

Figure 8:
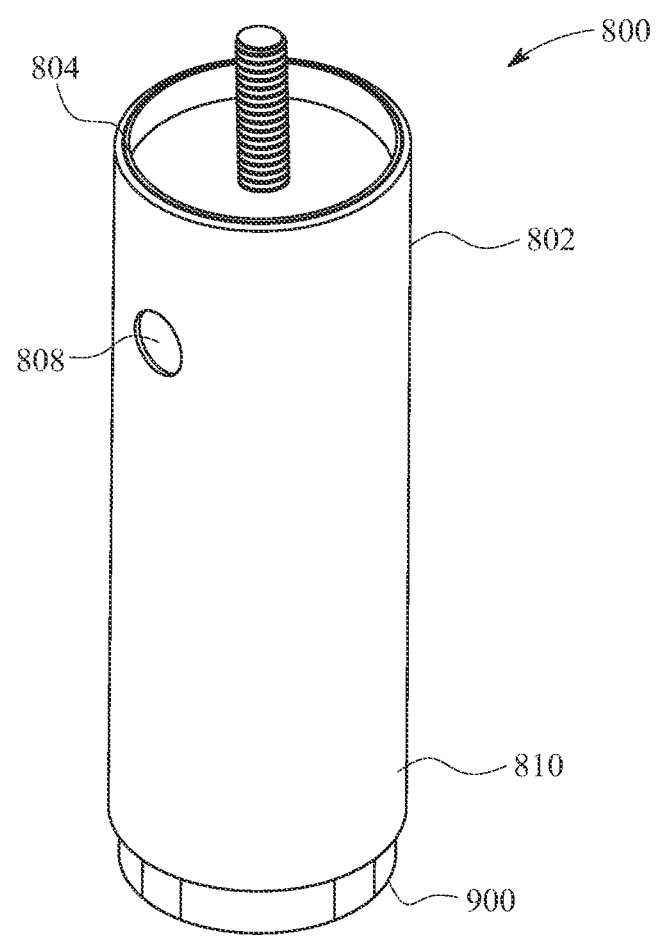
FIG. 8 is a top perspective view of a bed leg incorporating a sensor cartridge as disclosed herein.

FIG. 8 illustrates an assembly 800 that has another embodiment of a sensor assembly 900 inserted into a leg 802 of the bed 100. The leg 802 is on an existing bed or may be purchased with a bed, already on the bed or a separate component that is selected with a frame. The leg shown is provided as an example only. A first end 804 of the leg 802 is configured to attached to the frame and/or substrate.

The sensor assembly 900 may be packaged as a cartridge that is configured to fit into the bottom of the leg 802. The sensor assembly may be disposed inside a cavity 806 that is defined by the leg 802. The cavity 806 may be existing in the leg 802 at the time of original manufacture of the leg or may be formed into a leg that does not have a cavity; i.e., the cavity 806 and the sensor assembly 900 can be retrofit to existing legs after the time of original manufacture. The sensor assembly 900 may be configured to support the leg 802 such that a distal end 810 of the leg 802 does not contact the floor. The leg 802 may have an aperture 808 anywhere in its side or top to surfaces to accommodate wiring if necessary.

Figure 9:
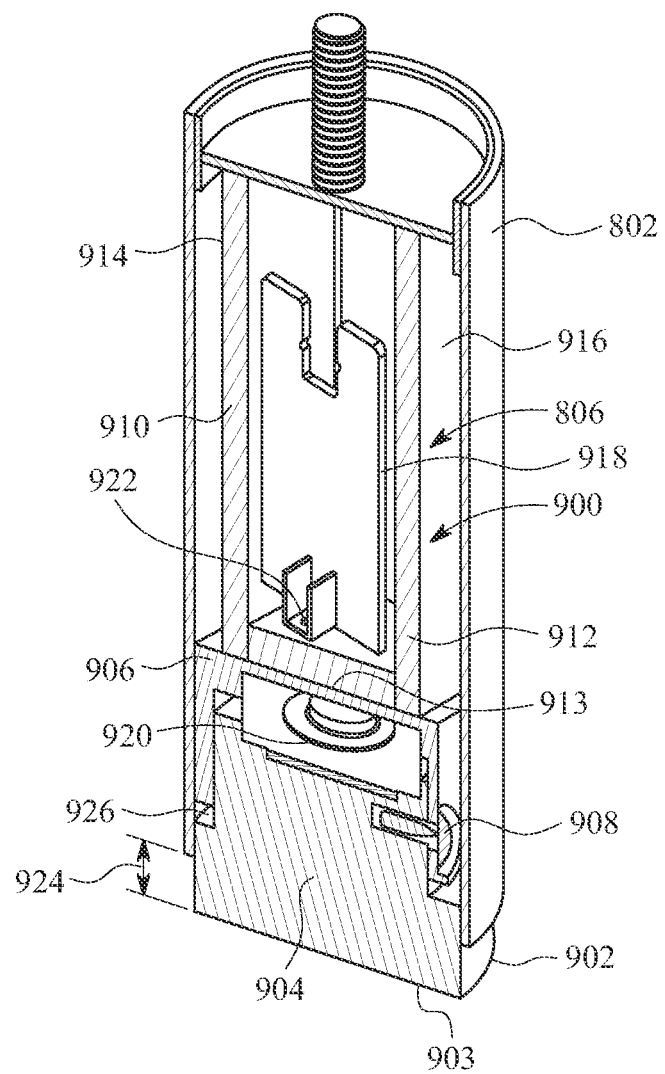
FIG. 9 is a cross-sectional view of the bed leg incorporating the sensor cartridge of FIG. 8.

FIG. 9 is cross-sectional view of FIG. 8. The sensor assembly 900 includes a base 902 having a first end portion 903 and a second end portion 904 opposite the first end portion 903. The base 902 is configured to provide contact with the floor at the first end portion 903. A cap 906 slides over the second end portion 904 of the base 902. The cap 906 may be attached to the base 902 using a screw 908, for example, to maintain radial alignment of the cap 906 and the base 902, so long as vertical movement is allowed between the cap 906 and the base 902. The sensor assembly 900 includes a load bearing member 910 having a third end portion 912 and a fourth end portion 914 opposite the third end portion 912. The load bearing member 910 defines a cavity 916. The third end portion 912 is in contact with the cap 906. The fourth end portion 914 is in contact with an interior portion of the leg 802 to transmit a load from the leg 802 to the sensor assembly 900. The cap 906 and the load bearing member 910 can be a single, integral piece.

The sensor assembly 900 includes a load sensor 920 between the cap 906 and the base 902. The load sensor 920 may include features similar to those of the load sensor 404 unless otherwise described. The load sensor 920 may be attached to the cap 906 and/or the base 902 via interference fit, adhesive, plastic welding, or any other means of attachment. The cap 906 may be configured to transmit the load from the leg 802 through the load bearing member 910 to the load sensor 920. The sensor assembly 900 includes a printed circuit board 918 disposed inside the cavity 916 defined by the load bearing member 910. The printed circuit board may have features similar to those of printed circuit board 500. The printed circuit board may be in wired or wireless communication with the load sensor 920. The cap 906 may include an aperture 922 through a portion of the cap 906 such that wiring may be routed through the aperture 922 from the load sensor 920 to the printed circuit board 918. If the cap 906 and load bearing member 910 are integral, i.e., no separate cap 906, a wall 913 may be configured in the load bearing member 910 to translate the force to the load sensor 920 as well as have means to retain the printed circuit board 918.

When the subject sits, lies, or moves on the substrate, the load from the subject is transferred through each contact with the floor (i.e., ground). The load is transferred from the leg 802 to the sensor assembly 900. Specifically, the load may be transferred from the leg 802 to the load bearing member 910 via contact between the leg 802 and the fourth end portion 914 of the load bearing member 910. The load bearing member 910 transfers the load to the cap 906. The cap 906 transfers the load to the load sensor 920. The substrate leg 802 is configured to move vertically relative to the base 902 as the magnitude of the load on the substrate changes. A gap 924 between the leg 802 and the floor facilitates the vertical movement of the leg 802 relative to the base 902. A gap 926 between the cap 906 and the base 902 allows for vertical movement between the cap 906 and the base 902.

Figure 10:
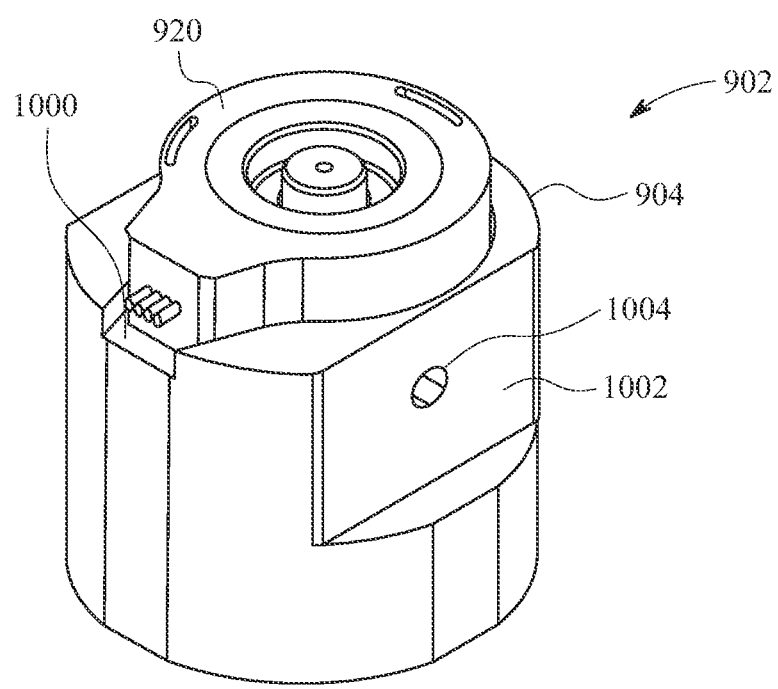
FIG. 10 is a top perspective view of a base of the sensor cartridge of FIG. 8.

FIG. 10 is a top perspective view of the base 902. The base 902 may have a shape profile that cooperates with the shape of the leg 802. As illustrated, the base 902 has a substantially cylindrical shape as does the leg 802. However, the base 902 may be a square, rectangular, or any other shape so long as it fits into the leg 802. The second end portion 904 of the base 902 may include a recess 1000 defined in the second end portion 904 of the base 902. The recess 1000 may be configured to receive the load sensor 920. For example, an interior profile of the recess 1000 in the base 902 may be shaped to correspond with an exterior profile of a portion of the load sensor 920. In this configuration, the load sensor 920 and the base 902 may be configured to fit together to maintain alignment of the load sensor 920 and the base 902. The base 902 is configured to receive the cap 906 over at least a portion of the base 902, and may include one or more cut outs shaped to receive the cap 906. In the illustrated, non-limiting example, the base 902 includes two opposing flat portions 1002 located on a periphery of the base 902. The opposing flat portions 1002 may be shaped to receive flanges of the cap 906. The base 902 may also include one or more aperture 1004 configured to receive a fastener (e.g. screw) to attach the cap 906 to the base 902. In other embodiments, any portion of the base 902 may be shaped in any way to receive the cap 906.

Figure 11A:
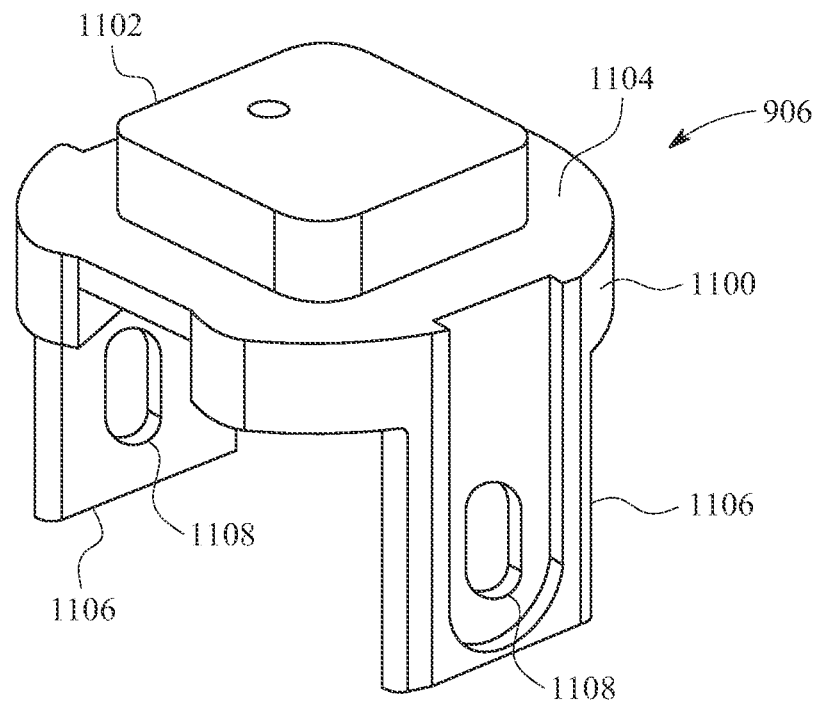
FIG. 11A is a top perspective view of a cap of the sensor cartridge of FIG. 8.
Figure 11B:
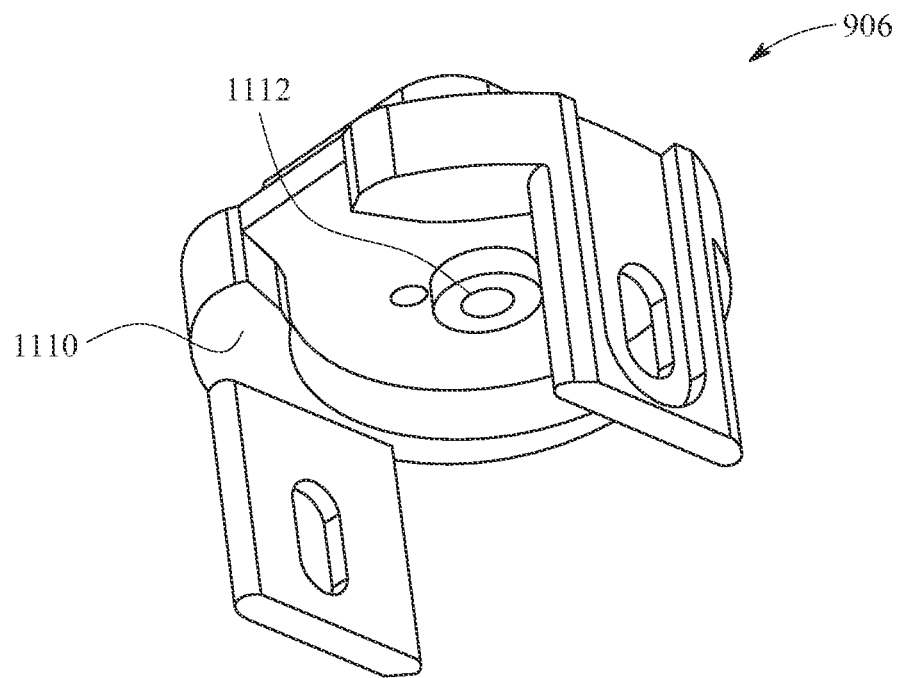
FIG. 11B is a bottom perspective view of the cap of the sensor cartridge of FIG. 11A.

FIGS. 11A and 11B illustrate the cap 906. The cap 906 may include a bottom portion 1100 and a top portion 1102. The top portion 1102 is configured to hold the printed circuit board 918 in the cavity 916 of the load bearing member 910. The top portion 1102 may have an exterior profile shaped to correspond with an interior profile of the load bearing member 910. In the illustrated, non-limiting example, the top portion 1102 includes a rectangular shape such that the top portion 1102 may be received inside a load bearing member 910 having a rectangular and tubular shape. In other embodiments, the top portion 1102 and the load bearing member 910 may include any other shape. The third end portion 912 of the load bearing member 910 may contact a top surface 1104 of the bottom portion 1100. The bottom portion 1100 is configured to slide over the base 902. For example, the cap 906 may include two flanges 1106 disposed on opposing sides of the bottom portion 1100 configured to slide over a portion of the base 902 (e.g. the flat portions 1002 of the base 902). The flanges 1106 may each include an aperture 1108 configured to receive a fastener (e.g. a screw) such that the cap 906 may be attached to the base 902. For example, the apertures 1108 may be aligned with the apertures 1004 so that a fastener can extend through the flanges 1106 and through a portion of the base 902. The apertures 1108 are shaped to allow for vertical movement of the cap 906 relative to the base 902. In other embodiments, the cap 906 may not include the flanges 1106 and the cap 906 may attach to the base 902 in any other suitable manner.

A bottom surface 1110 of the cap 906 has a contact member 1112 configured to contact the load sensor 920 of the base 902. In this configuration, the base 902, the cap 906, the load bearing member 910, and the load sensor 920 are configured to fit together to maintain radial alignment of the base 902, the cap 906, the load bearing member 910, and the load sensor 920. In other embodiments, load sensor 920 may be attached to the cap 906 with the contact member 1112 located on the base 902.

Figure 12:
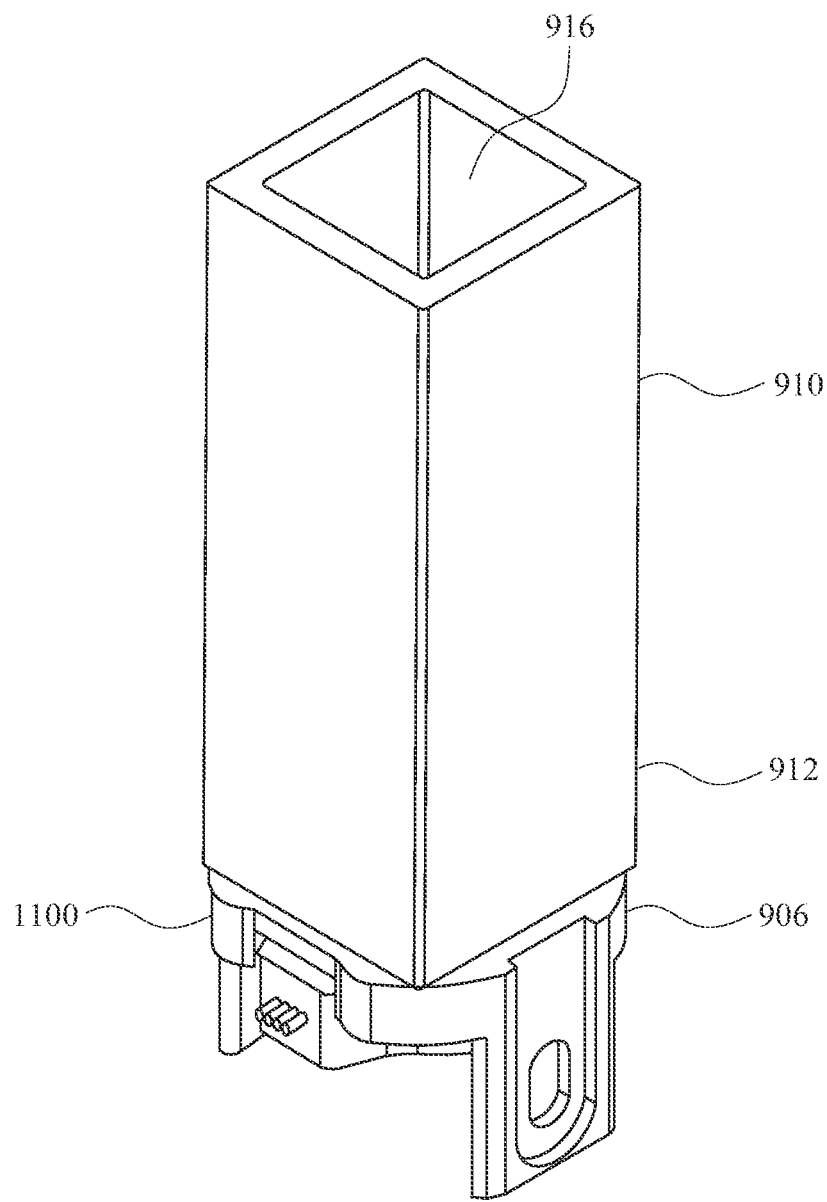
FIG. 12 is a top perspective view of a load bearing member and cap of the sensor cartridge of FIG. 8.

FIG. 12 is a top perspective view of the load bearing member 910 attached to the cap 906. In the illustrated, non-limiting example, the load bearing member 910 includes a rectangular tube that defines the cavity 916. The cavity 916 may be shaped to receive a portion of the cap 906 and the printed circuit board 918. The load bearing member 910 can be any alternative shape so long is it provides contact with the leg 802 and evenly distributes the load. For example, the load bearing member 910 may a cylindrical tube, a cylinder having a portion that is solid, two or more walls, two or more columns or any other shape, configuration, and orientation.

Figure 13:
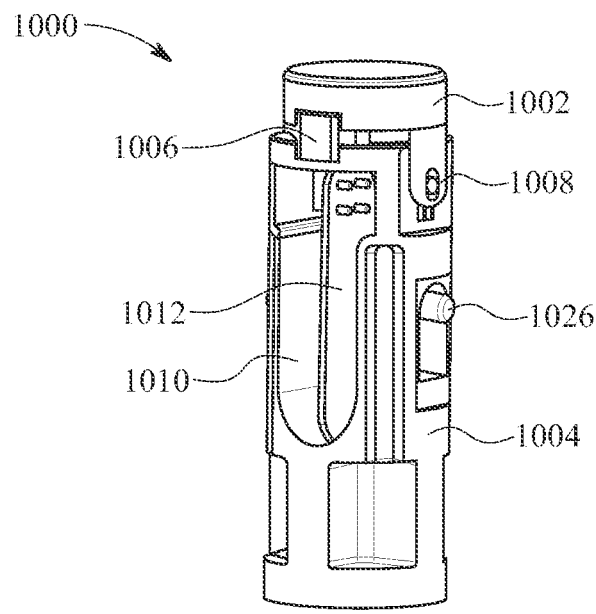
FIG. 13 is a perspective view of another sensor assembly as disclosed herein.

FIG. 13 is another example of a sensor assembly 1000 that can be used as either a cartridge that is slid into an existing leg of a bed or can include a sleeve and means of attachment to the frame/substrate. The sensor assembly includes a load bearing member 1002 and a base 1004 configured to contact a floor. A load sensor 1006 is positioned between the load bearing member 1002 and the base 1004. The load bearing member 1002 is attached to the base 1004 in such a way that vertical movement is allowed of the load bearing member 1002 but lateral or radial movement is restrained. As shown, one means of this attachment 1008 is a fastener that threads both the load bearing member 1002 and the base 1004, while the base 1004 has an aperture that allows vertical movement of the fastener and the load bearing member 1002 has an aperture that is sized to tightly fit the aperture. A cavity 1010 is provided in the base 1002 to hold a printed circuit board 1012. However, the printed circuit board 1012 can be held within a cavity of the load bearing member 1002 as well.

The load sensor 1006 will be attached to one of the load bearing member 1002 and the base 1004, with the other of the load bearing member or the base having a sensor contact that is configured to contact the load sensor 106 and transfer the load to the load sensor 1006.

Figure 14:
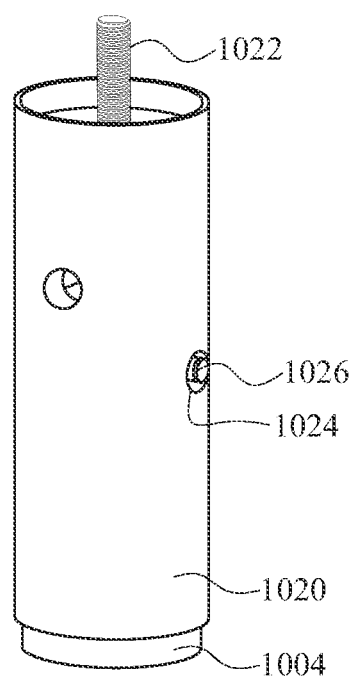
FIG. 14 is a perspective view of the sensor assembly of FIG. 13 used as a cartridge.

The base 1004 and load bearing member 1002 have exterior profiles that will slide into an existing leg of a bed. However, this exterior profile is not necessary and can be of any exterior profile so long as the base 1004 is in contact with the floor and the load is properly transferred from the load bearing member 1002 to the load sensor 1006. As illustrated in FIG. 14, the sensor assembly 1000 can slide into an existing leg 1020 having an existing attachment 1022 for attachment to the frame or substrate. The existing leg 1020 can have an aperture 1024 that is configured to receive a peg 1026 in the sensor assembly 100 that can be retracted while the sensor assembly 1000 is slide into the existing leg 1020 and pop out when aligned with the aperture 1024 to hold the sensor assembly 1000 in place within the leg 1020. Note that the existing leg 1020 does not contact the floor. Only the base 1004 of the sensor assembly 1000 contacts the floor.

Figure 15:
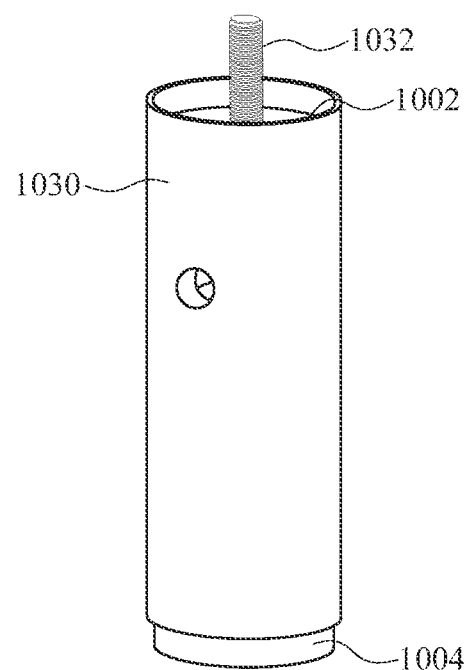
FIG. 15 is a perspective view of the sensor assembly of FIG. 13 used as the bed leg itself.

Alternatively, as illustrated in FIG. 15, the sensor assembly 1000 can be the bed leg and can include a sleeve 1030 that is integral with the base 1004 or that covers the base 1004 and the load bearing member 1002 for aesthetic purposes. The load bearing member 1002 can include an attachment member 1032 that attaches to the frame or substrate.

Examples of data determinations that can be made using the systems herein are described. The algorithms are dependent on the number of sensors and each sensor's angle and distance with respect to the other sensors. This information is predetermined. Software algorithms will automatically and continuously maintain "empty weight" calibration with the sensors so that any changing in weight due to changes in a mattress or bedding is accounted for.

The load sensor assemblies herein utilize macro signals and micro signals and process those signals to determine a variety of data, described herein. Macro signals are low frequency signals and are used to determine weight and center of mass, for example. The strength of the macro signal is directly influence by the subject's proximity to each sensor.

Micro signals are also detected due to the heartbeat, respiration and to movement of blood throughout the body. Micro signals are higher frequency and can be more than 1000 times smaller than macro signals. The sensors detect the heart beating and can use this amplitude data to determine where on the substrate the heart is located, thereby assisting in determining in what direction and position the subject is laying. In addition, the heart pumps blood in such a way that it causes top to bottom changes in weight. There is approximately seven pounds of blood in a human subject, and the movement of the blood causes small changes in weight that can be detected by the sensors. These directional changes are detected by the sensors. The strength of the signal is directly influenced by the subject's proximity to the sensor. Respiration is also detected by the sensors. Respiration will be a different frequency than the heart beat and has different directional changes than those that occur with the flow of blood. Respiration can also be used to assist in determining the exact position and location of a subject on the substrate. These bio-signals of heart beat, respiration and directional movement of blood are used in combination with the macro signals to calculate a large amount of data about a subject, including the relative strength of the signal components from each of the sensors, enabling better isolation of a subject's bio-signal from noise and other subjects.

As a non-limiting example, the cardiac bio-signals in the torso area are out of phase with the signals in the leg regions. This allows the signals to be subtracted which almost eliminates common mode noise while allowing the bio-signals to be combined, increasing the signal to noise by as much as a factor of 3 db or 2× and lowering the common or external noise by a significant amount. By analyzing the phase differences in the 1 hz to 10 hz range (typically the heart beat range) the angular position of a person laying on the bed can be determined. By analyzing the phase differences in the 0 to 0.5 hz range, it can be determined if the person is supine or laying on their side, as non-limiting examples.

Because signal strength is still quite small, the signal strength can be increased to a level more conducive to analysis by adding or subtracting signals, resulting in larger signals. The signal deltas are combined in signal to increase the signal strength for higher resolution algorithmic analysis.

The controller can be programmed to cancel out external noise that is not associated with the subject laying on the bed. External noise, such as the beat of a bass or the vibrations caused by an air conditioner, register as the same type of signal on all sensor assemblies and is therefore canceled out when deltas are combined during processing.

Using superposition analysis, two subjects can be distinguished on one substrate. Superposition simplifies the analysis of the signal with multiple inputs. The usable signal equals the algebraic sum of the responses caused by each independent sensor acting alone. To ascertain the contribution of each individual source, all of the other sources first must be turned off, or set to zero. This procedure is followed for each source in turn, then the resultant responses are added to determine the true result. The resultant operation is the superposition of the various sources. By using signal strength and out-of-phase heart rates, individuals can be distinguished on the same substrate.

The controller can be programmed to provide provide dynamic center of mass location and movement vectors for the subject, while eliminating those from other subjects and inanimate objects or animals on the substrate. By leveraging multiple sensor assemblies that detect the z-axis of the force vector of gravity, and by discriminating and tracking the center of mass of multiple subjects as they enter and move on a substrate, not only can presence, motion and cardiac and respiratory signals for the subject be determined, but the signals of a single or multiple subjects on the substrate can be enhanced by applying the knowledge of location to the signal received. By analyzing the bio-signal's amplitude and phase in different frequency bands, the center of mass for a subject can be obtained using multiple methods, examples of which include:

DC weight;

AC low band analysis of signal, center of mass and back supine respiratory identification of subject;

AC mid band analysis of signal center of mass and cardiac identification of subject; and AC upper mid band identification of snorer or apnea events.

The data from the load sensor assemblies can be used to determine presence and location X, Y, theta, back and supine positions of a subject on a substrate. Such information is useful for calculating in/out statistics for a subject such as: period of time spent in bed, time when subject fell asleep, time when subject woke up, time spent on back, time spent on side, period of time spent out of bed. The sensor assemblies can be in sleep mode until the presence of a subject is detected on the substrate, waking up the system.

Macro weight measurements can be used to measure the actual static weight of the subject as well as determine changes in weight over time. Weight loss or weight gain can be closely tracked as weight and changes in weight can be measured the entire time a subject is in bed every night. This information may be used to track how different activities or foods affect a person's weight. For example, excessive water retention could be tied to a particular food. In a medical setting, for example, a two-pound weight gain in one night or a five-pound weight gain in one week could raise an alarm that the patient is experiencing congestive heart failure. Unexplained weight loss or weight gain can indicate many medical conditions. The tracking of such unexplained change in weight can alert professionals that something is wrong.

Center of mass can be used to accurately heat and cool particular and limited space in a substrate such as a mattress, with the desired temperature tuned to the specific subject associated with the center of mass, without affecting other subjects on the substrate. Certain mattresses are known to provide heating and/or cooling. As non-limiting examples, a subject can set the controller to actuate the substrate to heat the portion of the substrate under the center of mass when the temperature of the room is below a certain temperature. The subject can set the controller to instruct the substrate to cool the portion of the substrate under the center of mass when the temperature of the room is above a certain temperature.

These macro weight measurements can also be used to determine a movement vector of the subject. Subject motion can be determined and recorded as a trend to determine amount and type of motion during a sleep session. This can determine a general restlessness level as well as other medical conditions such as "restless leg syndrome" or seizures.

Motion detection can also be used to report in real time a subject exiting from the substrate. Predictive bed exit is also possible as the position on the substrate as the subject moves is accurately detected, so movement toward the edge of a substrate is detected in real time. In a hospital or elder care setting, predictive bed exit can be used to prevent falls during bed exit, for example. An alarm might sound so that a staff member can assist the subject exit the substrate safely.

Data from the load sensor assemblies can be used to detect actual positions of the subject on the substrate, such as whether the subject is on its back, side, or stomach, and whether the subject is aligned on the substrate vertically, horizontally, with his or her head at the foot of the substrate or head of the substrate, or at an angle across the substrate. The sensors can also detect changes in the positions, or lack thereof. In a medical setting, this can be useful to determine if a subject should be turned to avoid bed sores. In a home or medical setting, firmness of the substrate can be adjusted based on the position of the subject. For example, sleeping angle can be determined from center of mass, position of heart beat and/or respiration, and directional changes due to blood flow.

Controlling external devices such as lights, ambient temperature, music players, televisions, alarms, coffee makers, door locks and shades can be tied to presence, motion and time, for example. As one example, the controller can collect signals from each load sensor assembly, determine if the subject is asleep or awake and control at least one external device based on whether the subject is asleep or awake. The determination of whether a subject is asleep or awake is made based on changes in respiration, heart rate and frequency and/or force of movement. As another example, the controller can collect signals from each load sensor assembly, determine that the subject previously on the substrate has exited the substrate and change a status of the at least one external device in response to the determination. As another example, the controller can collect signals from each load sensor assembly, determine that the subject has laid down on the substrate and change a status of the at least one external device in response to the determination.

A light can be automatically dimmed or turned off by instructions from the controller to a controlled lighting device when presence on the substrate is detected. Electronic shades can be automatically closed when presence on the substrate is detected. A light can automatically be turned on when bed exit motion is detected or no presence is detected. A particular light, such as the light on a right side night stand, can be turned on when a subject on the right side of the substrate is detected as exiting the substrate on the right side. Electronic shades can be opened when motion indicating bed exit or no presence is detected. If a subject wants to wake up to natural light, shades can be programmed to open when movement is sensed indicating the subject has woken up. Sleep music can automatically be turned on when presence is detected on the substrate. Predetermined wait times can be programmed into the controller, such that the lights are not turned off or the sleep music is not started for ten minutes after presence is detected, as non-limiting examples.

The controller can be programmed to recognize patterns detected by the load sensor assemblies. The patterned signals may be in a certain frequency range that falls between the macro and the micro signals. For example, a subject may tap the substrate three times with his or her hand, creating a pattern. This pattern may indicate that the substrate would like the lights turned out. A pattern of four taps may indicate that the subject would like the shades closed, as non-limiting examples. Different patterns may result in different actions. The patterns may be associated with a location on the substrate. For example, three taps near the top right corner of the substrate can turn off lights while three taps near the base of the substrate may result in a portion of the substrate near the feet to be cooled. Patterns can be developed for medical facilities, in which a detected pattern may call a nurse.

While the figures all illustrate the use of the sensor assemblies with a bed as a substrate, it is contemplated that the sensor assemblies can be used with chairs such as desks, where a subject spends extended periods of time. A wheel chair can be equipped with the sensors to collect signals and provide valuable information about a patient. The sensors may be used in an automobile seat and may help to detect when a driver is falling asleep or his or her leg might go numb. Furthermore, the bed can be a baby's crib, a hospital bed, or any other kind of bed.

Implementations of controller 200 and/or controller 214 (and the algorithms, methods, instructions, etc., stored thereon and/or executed thereby) can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors or any other suitable circuit. In the claims, the term "controller" should be understood as encompassing any of the foregoing hardware, either singly or in combination.

Further, in one aspect, for example, controller 200 and/or controller 214 can be implemented using a general purpose computer or general purpose processor with a computer program that, when executed, carries out any of the respective methods, algorithms and/or instructions described herein. In addition or alternatively, for example, a special purpose computer/processor can be utilized which can contain other hardware for carrying out any of the methods, algorithms, or instructions described herein.

The word "example," "aspect," or "embodiment" is used herein to mean serving as an example, instance, or illustration. Any aspect or design described herein as using one or more of these words is not necessarily to be construed as preferred or advantageous over other aspects or designs. Rather, use of the word "example," "aspect," or "embodiment" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A load sensor assembly for a substrate that supports a subject, the load sensor assembly comprising:
   at least four substrate support members, wherein each of the four substrate support members comprises:
   a bed leg configured to be attached to the substrate at a first end of the bed leg;
   a base configured to support the bed leg and to provide contact with a floor, wherein the base and the bed leg are configured to fit together to maintain lateral alignment of the base and the bed leg while the bed leg is configured to move vertically relative to the base;
   a load sensor between the bed leg and the base, wherein the bed leg is configured to transmit a load from the substrate to the load sensor; and
   a printed circuit board positioned in a cavity defined by the bed leg, the printed circuit board in communication with the load sensor, wherein the printed circuit board is configured to receive and process data from the load sensor.

2. The load sensor assembly of claim 1, wherein the load sensor is attached to at least one of the bed leg or the base, and wherein at least one of the bed leg or the base includes a recess configured to receive the load sensor.

3. The load sensor assembly of claim 1, wherein the bed leg defines the cavity and includes a cap at a second end of the bed leg, and wherein the cap is configured to hold the printed circuit board within the cavity.

4. The load sensor assembly of claim 1, wherein the base includes a sleeve disposed around the bed leg.

5. The load sensor assembly of claim 1, comprising a controller in communication with the printed circuit board, wherein the controller is configured to output power to the printed circuit board and the load sensor, to process data output by the printed circuit board, and to transmit the processed data to an external device.

6. The load sensor assembly of claim 1, comprising eight support members, wherein the substrate is configured to support two subjects.

7. The load sensor assembly of claim 1, comprising nine support members, wherein the substrate is configured to support two subjects.

8. A sensor cartridge for use with a bed, the cartridge comprising:
   a base having a first end portion and a second end portion opposite the first end portion, wherein the base is configured to provide contact with a floor at the first end portion;
   a bed leg engaged with the second end portion of the base, wherein the base and the bed leg are configured to fit together to maintain lateral alignment of the bed leg to the base while allowing vertical movement of the bed leg with respect to the base;

a load sensor between the bed leg and the base, wherein the bed leg is configured to transmit the load from a substrate to the load sensor; and a printed circuit board positioned within a cavity defined by the bed leg, the printed circuit board in communication with the load sensor and configured to receive and process data from the load sensor, wherein the sensor cartridge is configured to insert into an element of the bed that is at least partially hollow.

9. The cartridge of claim 8, wherein the load sensor is attached to at least one of the bed leg or the base, and wherein at least one of the second end portion of the base or a bottom surface of the bed leg includes a recess to receive the load sensor.

10. The cartridge of claim 8, wherein the printed circuit board is in communication with a controller configured to do one or more of output power to the printed circuit board and the load sensor, receive and process data output by the printed circuit board, and transmit the processed data to an external device.

11. The cartridge of claim 8, wherein the bed leg comprising a wall positioned between the load sensor and the cavity and having a means of retaining the printed circuit board opposite the load sensor.

12. The cartridge of claim 8, wherein the first end portion of the base is configured to be in contact with the floor while the bed leg is not in contact with the floor.

13. A bed having a frame supporting a substrate configured to support a subject, the bed comprising:

substrate support members, each substrate support member comprising:

a load bearing member having a first end portion and a second end portion;

a base configured to provide contact with a floor, wherein the load bearing member is configured to move vertically relative to the base and the base and the load bearing member are configured to fit together to maintain lateral alignment of the base and the load bearing member;

a load sensor between the load bearing member and the base, wherein the load bearing member is configured to transmit a load from the substrate to the load sensor; and a printed circuit board in communication with the load sensor, wherein the printed circuit board is configured to receive and process data from the load sensor; and a controller in communication with the printed circuit board of each substrate support member, wherein the controller is configured to receive and process data output by the printed circuit boards, the bed further comprising at least four legs, wherein:

each substrate support member is a cartridge configured to be inserted into a leg that is at least partially hollow such that a first end portion of the load bearing member contacts a horizontal surface of the leg.

14. The bed of claim 13, wherein the cartridge is configured to be inserted into the leg such that the base is in contact with the floor while the leg is not in contact with the floor.

* * * * *